US010053436B2

(12) United States Patent
Gebhardt et al.

(10) Patent No.: US 10,053,436 B2
(45) Date of Patent: Aug. 21, 2018

(54) PROCESS FOR THE PREPARATION OF SUBSTITUTED OXIRANES AND TRIAZOLES

(71) Applicant: BASF Agro B.V., Arnhem (NL)

(72) Inventors: Joachim Gebhardt, Ludwigshafen (DE); Manfred Ehresmann, Maxdorf (DE); Tiziana Chiodo, Mannheim (DE); Martin Viertelhaus, Mannheim (DE); Roland Goetz, Neulussheim (DE)

(73) Assignee: BASF Agro B.V., Arnhem (NL)

( * ) Notice: Subject to any disclaimer, the term of this patent is extended or adjusted under 35 U.S.C. 154(b) by 0 days.

(21) Appl. No.: 15/324,312

(22) PCT Filed: Jun. 26, 2015

(86) PCT No.: PCT/EP2015/064550
§ 371 (c)(1),
(2) Date: Jan. 6, 2017

(87) PCT Pub. No.: WO2016/005211
PCT Pub. Date: Jan. 14, 2016

(65) Prior Publication Data
US 2017/0166540 A1 Jun. 15, 2017

(30) Foreign Application Priority Data
Jul. 8, 2014 (EP) ..................................... 14176130

(51) Int. Cl.
*C07D 295/096* (2006.01)
*C07D 249/08* (2006.01)
*C07D 301/02* (2006.01)
*C07D 303/38* (2006.01)

(52) U.S. Cl.
CPC ....... *C07D 295/096* (2013.01); *C07D 249/08* (2013.01); *C07D 301/02* (2013.01); *C07D 303/38* (2013.01)

(58) Field of Classification Search
None
See application file for complete search history.

(56) References Cited

U.S. PATENT DOCUMENTS

| 4,898,954 A | 2/1990 | Mohrmann et al. |
| 4,945,100 A | 7/1990 | Nyfeler et al. |
| 4,992,458 A | 2/1991 | Riebli et al. |
| 5,143,932 A | 9/1992 | Jautelat et al. |

FOREIGN PATENT DOCUMENTS

| CA | 1171866 | 7/1984 |
| CA | 1209152 | 8/1986 |
| DE | 3042302 | 8/1981 |
| DE | 3315681 | 10/1984 |
| DE | 3733755 | 4/1989 |
| DE | 4003180 | 8/1991 |
| EP | 0113640 | 7/1984 |
| EP | 0126430 | 11/1984 |
| EP | 0275955 | 7/1988 |
| EP | 0735142 | 2/1996 |
| WO | 2002085891 | 10/2002 |
| WO | 2013010862 | 1/2013 |
| WO | WO 2013007767 | 1/2013 |
| WO | WO 2013066360 | 5/2013 |
| WO | WO 2013124791 | 8/2013 |
| WO | WO 2013189910 | 12/2013 |
| WO | WO 2014012811 | 1/2014 |
| WO | WO 2014026845 | 2/2014 |
| WO | WO 2014026893 | 2/2014 |
| WO | WO 2014026928 | 2/2014 |
| WO | WO 2014060449 | 4/2014 |
| WO | WO 2014108286 | 7/2014 |
| WO | WO 2014111398 | 7/2014 |
| WO | WO 2014135392 | 9/2014 |
| WO | WO 2014155214 | 10/2014 |
| WO | WO 2014202589 | 12/2014 |
| WO | WO 2015011119 | 1/2015 |
| WO | WO 2015011120 | 1/2015 |
| WO | WO 2015055447 | 4/2015 |
| WO | WO 2015086596 | 6/2015 |
| WO | WO 2015091045 | 6/2015 |
| WO | WO 2015158518 | 10/2015 |
| WO | WO 2015169883 | 11/2015 |
| WO | WO 2016001025 | 1/2016 |

OTHER PUBLICATIONS

Afon'Kin et al., "Synthesis of Some Electron-Rich Aryl(hetaryl)oxiranes under Phase-Transfer and Homogeneous Conditions," Russian Journal of Organic Chemistry, vol. 44, No. 12, (2008), pp. 1776-1779.

Corey and Chaykovsky, "Dimethyloxosulfonium Methylide ((CH3)2SOCH2) and Dimethylsulfonium Methylide ((CH3)2SCH2). Formation and Application to Organic Synthesis," Journal of American Chemical Society, vol. 87, No. 6, (1965), pp. 1353-1364.

International Preliminary Report on Patentability, issued in PCT/EP2015/064550, dated.

International Search Report, issued in PCT/EP2015/064550, dated Dec. 16, 2015.

Mosset and Grée, "Trimethylsulfonium Methylsulfate, a Simple and Efficient Epoxidizing Agent," Synthetic Communications, vol. 15, No. 8, (1985), pp. 749-757.

(Continued)

*Primary Examiner* — Alicia L Otton
(74) *Attorney, Agent, or Firm* — Brinks Gilson & Lione

(57) ABSTRACT

The present invention relates to a process for the preparation of oxirane compounds of formula II from keto compounds III using dimethyl sulfide $(CH_3)_2S$ and dimethylsulfate $(CH_3)_2SO_4$, forming the reagent IV, trimethylsulfonium methylsulfate $[(CH_3)_3S^+ \, CH_3SO_4^-]$, in aqueous solution in the presence of potassium hydroxide (KOH).

7 Claims, 6 Drawing Sheets

(56) References Cited

OTHER PUBLICATIONS

Yu et al., "Synthesis and Fungicidal Evaluation of 2-Arylphenyl Ether-3-(1H-1,2,4-triazol-l-yl)propan-2-ol Derivatives," J. Agric. Food Chem., vol. 57, No. 11, (2009), pp. 4854-4860.
Brandes and Jacobsen, "Synthesis of Enantiopure 3-chlorostyrene Oxide via an Asymmetric Epoxidation-Hydrolytic Kinetic Resolution Sequence," Tetrahedron:Asymmetry, vol. 8, No. 23, (1997), pp. 3927-3933.
Forrester et al., "Generation of Trimethylsulfonium Cation from Dimethyl Sulfoxide and Dimethyl Sulfate: Implications for the Synthesis of Epoxides from Aldehydes and Ketones," J. Chem. Soc. Perkin Trans. (1995), pp. 2289-2291.
Kuzenkov, "Synthesis of Substituted 2-azolyl-1-pyridylethan-1-ols," Chemistry of Heterocyclic Compounds, vol. 39, No. 11, (2003), pp. 1492-1495.

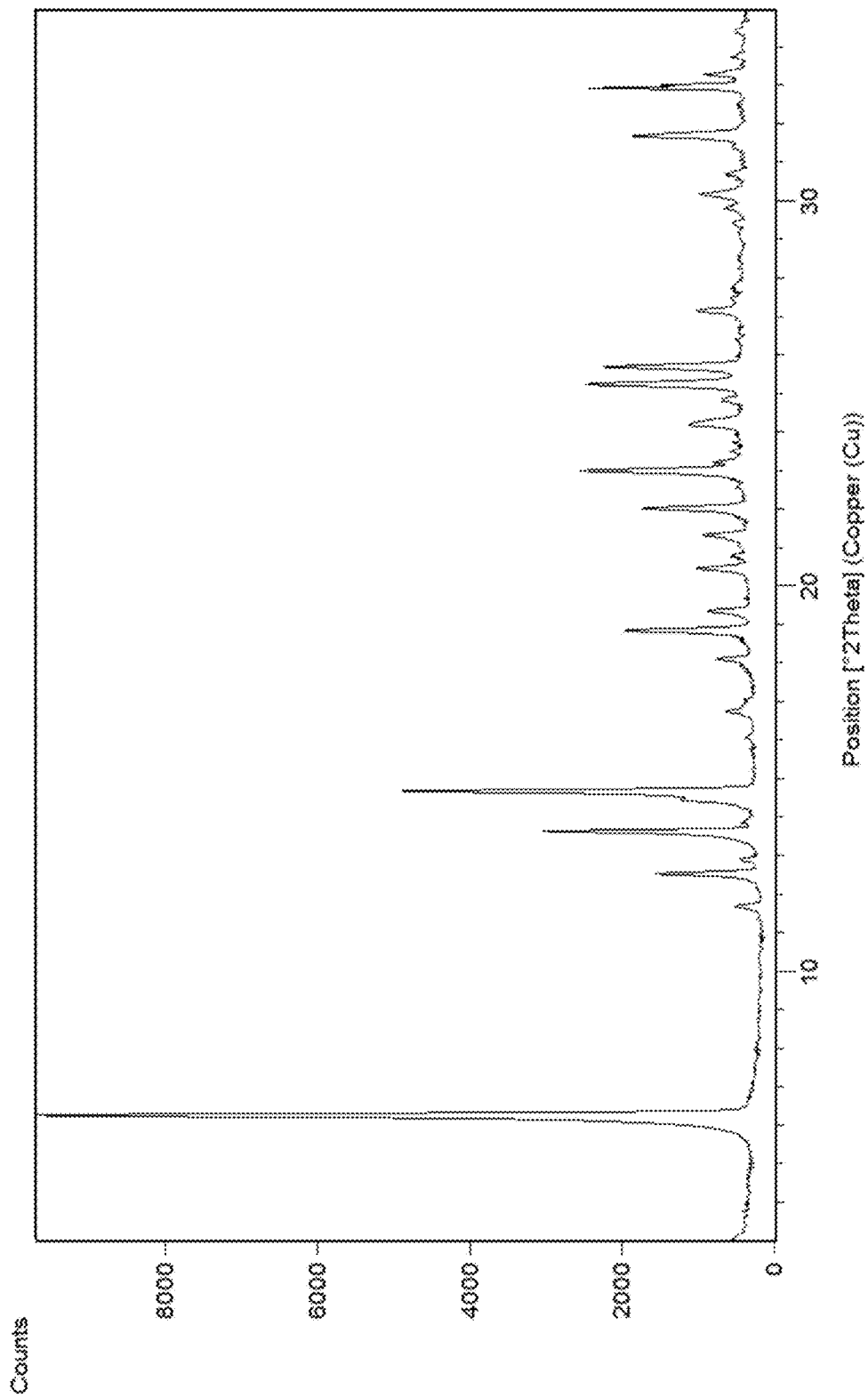

PROCESS FOR THE PREPARATION OF SUBSTITUTED OXIRANES AND TRIAZOLES

This application is a National Stage application of International Application No. PCT/EP2015/064550, filed Jun. 26, 2015. This application also claims priority under 35 U.S.C. § 119 to European Patent Application No. 14176130.4, filed Jul. 8, 2014.

The present invention relates to a process for providing oxiranes comprising reacting a respective ketone with dimethylsulfate $(CH_3)_2SO_4$ and dimethyl sulfide $(CH_3)_2S$ in aqueous solution in the presence of potassium hydroxide (KOH), wherein dimethyl sulfide and dimethyl sulfate are used in a molar ratio of 1:1 to 2:1, and wherein apart from the reagents used at most 10 weight-% organic solvent in relation to the amount of compound III are added. Further, the present invention relates to a process for converting the resulting oxiranes into triazole compounds by reacting the substituted oxiranes with 1H-1,2,4-triazole under basic conditions.

The substituted oxiranes provided by the process according to the present invention are valuable intermediate compounds for the synthesis of triazole compounds having pesticidal, in particular fungicidal activity. WO 2013/007767 (PCT/EP2012/063626) is directed to fungicidal substituted 2-[2-halogenalkyl-4-phenoxy-phenyl]-1-[1,2,4]triazol-1-yl-ethanol compounds, that can be synthesized via a respective oxirane intermediate compound. A common process for the synthesis of oxiranes from carbonyl compounds such as aldehydes and ketones is the reaction with trimethylsulfonium iodide in the presence of a base (JACS 1965, 87, p 1353ff). This reagent is very expensive and not suitable for industrial scales.

Synthetic Communications 15, 1985, p. 749ff. generally describes the reaction of trimethylsulfonium methyl sulfate with aldehydes and ketones using 50% NaOH solution. However, not with every ketone or aldehyde, satisfying yields can be achieved, in particular, aldehydes that are more reactive are reacted. According to this document, NaOH is used as base for the reaction and high amounts of water are used because the base is added as 50% aqueous solution. Furthermore, high excess of base and preferably methylenechloride are used in the process, which is not suitable for an industrial process also because of environmental issues. A. A. Afonkin et al. In the Russian Journal of Organic Chemistry, vol. 44, no. 12, 2008, pp 1776 to 1779, is directed to the synthesis of some electron-rich aryl (heteroaryl) oxiranes under phase-transfer and homogenous conditions using trimethylsulfonium methyl sulfate as reagent. In this reference, the reaction of aldehydes is described that are generally more reactive than ketones. NaOH is used as 50% aqueous solution.

DE 3315681 is directed to a process for the preparation of certain oxiranes from ketones using trimethylsulfonium methylsulfate in the presence of tert-butanol as organic solvent and a base, such as Kalium-tert-butylate.

DE3733755 is directed to a process for the preparation of 2-(4-chlorophenyl-ethyl)-2-tert-butyloxirane from the respective ketone using trimethylsulfonium methylsulfate in the presence of potassium hydroxide, dimethylsulfide and water. According to this document, dimethylsulfide is used in excess as organic solvent. The disadvantage of the use of great amounts of organic solvents such as dimethyl sulfide is that after completion of the reaction such solvents have to be removed from the reaction mixture. Furthermore larger reaction and work up equipment is needed.

WO 2014/108286 (PCT/EP2013/077083) is directed to an improved process for the preparation of oxiranes from ketones using trimethylsulfonium methylsulfate.

The methods known from the literature are sometimes not suitable for the efficient synthesis of substituted oxiranes because the yield is not sufficient and/or the reaction conditions and parameters such as the use of solvents and/or the proportion of the reactants and ingredients to each other are not suitable for an upscale to industrially relevant amounts. Inter alia because some oxiranes are valuable intermediates for the synthesis of triazole compounds with promising fungicidally activity, there is an ongoing need for improved processes that easily make such intermediates and compounds available.

An object of the present invention was to provide an improved process for the synthesis of oxiranes that are valuable intermediates for the preparation of fungicidal active triazole compounds starting from the respective oxo-group containing compounds. Furthermore, the object underlying the present invention was to optimize the synthesis of triazole active compounds using said oxiranes.

It has now surprisingly been found a highly efficient synthesis for the conversion of specific oxo-group containing compounds into oxiranes that are useful as intermediates in the synthesis of certain pesticidal triazole compounds.

Accordingly, one aspect of the present invention is a process for the preparation of the compounds of formula II

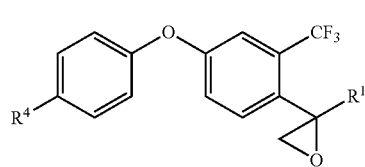

wherein
$R^1$ is $C_1$-$C_6$-alkyl or $C_3$-$C_8$-cycloalkyl; and
$R^4$ is F or Cl
comprising the following step:
(i) reacting an oxo compound of the formula III

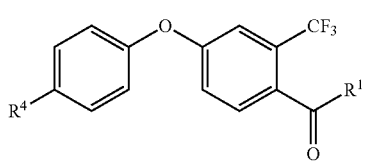

with dimethyl sulfide $(CH_3)_2S$ and dimethylsulfate $(CH_3)_2SO_4$, forming the reagent IV, trimethylsulfonium methylsulfate $[(CH_3)_3S^+ CH_3SO_4^-]$, in aqueous solution in the presence of potassium hydroxide (KOH), wherein dimethyl sulfide and dimethyl sulfate are used in a molar ratio of 1:1 to 2:1, and wherein at most 10 weight-% organic solvent in relation to the amount of compound III, are added.

Using the inventive process, less amounts of solvents are used than in conventional processes, which leads to smaller volumina of the reaction mixtures and higher space-time yields. Further, the inventive reaction allows faster conversion of the reagents to the desired products, which is favorable in particular with respect to industrial applicability.

In the process step (i) according to the present invention, an oxo compound of the formula III is reacted with dimethyl sulfide $(CH_3)_2S$ and dimethylsulfate $(CH_3)_2SO_4$, forming the reagent IV, trimethylsulfonium methylsulfate $[(CH_3)_3S^+ CH_3SO_4^-]$, in aqueous solution in the presence of potassium hydroxide (KOH), wherein dimethyl sulfide and dimethyl sulfate are used in a molar ratio of 1:1 to 2:1, and wherein at most 10 weight-% organic solvent in relation to the amount of compound III, are added apart from the reagents used.

In the oxo-compound III $R^1$ is $C_1$-$C_6$-alkyl or $C_3$-$C_8$-cycloalkyl; and $R^4$ is F or Cl. According to one embodiment, $R^1$ is $C_1$-$C_6$-alkyl, more specifically $C_1$-$C_4$-alkyl, in particular selected from $CH_3$, $C_2H_5$, n-$C_3H_7$, $CH(CH_3)_2$, n-butyl, iso-butyl and tert-butyl, more particularly selected from $CH_3$, $C_2H_5$, $CH(CH_3)_2$ and $C(CH_3)_3$. According to a further embodiment, $R^1$ is $C_3$-$C_8$-cycloalkyl, in particular $C_3$-$C_6$-cycloalkyl, such as $C_3H_5$ (cyclopropyl), $C_4H_7$ (cyclobutyl), cyclopentyl or cyclohexyl. A further embodiment relates to compounds, wherein $R^1$ is $C_3H_5$ (cyclopropyl) or $C_4H_7$ (cyclobutyl). $R^4$ is F or Cl, in particular Cl. In particular, $R^1$ is selected from $CH_3$, $CH(CH_3)_2$ and cyclopropyl and $R^4$ is Cl. The same applies for the variables $R^1$ and $R^4$ in compound II.

The reagent of formula IV is formed from dimethylsulfide and dimethylsulfate. In particular, reagent IV is prepared in-situ. Either dimethylsulfide or dimethylsulfate is charged first and the other reagent is then added. It may be preferred according to the invention to add dimethylsulfide to a reaction mixture containing dimethylsulfate.

The dimethylsulfide and dimethylsulfate are preferably used in such amounts that the reagent IV is present in the reaction mixture in an amount of 1.1 to 2.5, in particular 1.2 to 2, more specifically 1.3 to 1.6 equivalents of IV per 1 equivalent (mole) of compound III.

According to the inventive process, dimethylsulfide is used in amounts so that the reagent IV is sufficiently formed during the reaction. In the state of the art, it has been reported that the addition of a solvent such as tert-butanole or toluene or the use of dimethylsulfide in great excess is necessary. Dimethylsulfide in such cases acts as organic solvent. According to the invention, the molar ratio between dimethylsulfide and dimethylsulfate for the formation of the reagent IV is 1:1 to 2:1. Preferably, the molar ratio between dimethylsulfide and dimethylsulfate is 1:1 to 1.5:1, more preferably 1:1 to 1.4:1. It may be also preferred to use 1 to 1.3, in particular 1 to 1.25, more specifically 1 to 1.1 dimethylsulfide in relation to one equivalent of dimethylsulfate.

According to the inventive process apart from the reagents used, the reaction step (i) can surprisingly be carried out with very good results although at most 10 weight-% of organic solvents in relation to the amount of compound III are added [amount of solvent: (amount of solvent+amount of compound III)]. In particular, the reaction can be carried out using at most 8 weight-%, more specifically at most 5 weight-%, even more specifically at most 3 weight-%, of organic solvents in relation to the amount of compound III. More specifically, in the reaction mixture, at most 2 weight-%, more specifically at most 1 weight-% of organic solvents in relation to the amount of compound III are added.

In a specific embodiment, in the inventive process step (i) essentially no organic solvent is added. In particular, in the inventive process step (i) no organic solvent is added apart from the reagents used.

Thereby, the process for preparing oxiranes from keto compounds is simplified and an industrial application becomes more efficient.

Organic solvents are liquid organic compounds that dilute the reactants without taking part in the reaction or catalyzing the reaction. The skilled person in the field of organic synthesis is familiar with "organic solvents" and it is clear to such skilled person what kind of solvents are "organic solvents". Examples for organic solvents are e.g. alcohols, nitrils and aromatic hydrocarbons. Alcohols are for example methanol, ethanol, propanol and butanol (e.g. tert-butanol). Aromatic hydrocarbons are for example toluene or xylenes. An example for nitrile is acetonitrile.

Reaction step (i) is carried out in aqueous solution. Preferably, water is used in an amount of 0.5 to 4 eq, in particular 0.9 to 4, in relation to one equivalent of compound III. According to one embodiment of the invention, relatively low amounts of water, for example 0.5 to 0.95 eq, more specifically 0.6 to 0.94, even more specifically 0.7 to 0.93 eq in relation to one equivalent of compound III, are used. It may also be advantageous to use 0.8 to 0.92 eq, more specifically 0.85 to 0.91, even more specifically 0.85 to 0.9 eq in relation to one equivalent of compound III in the inventive process. According to a further embodiment, 0.9 to 4 equivalents, more specifically 1 to 4, in particular 1.2 to 3.5 eq, more specifically 1.5 to 3.3 eq, of water in relation to one equivalent of compound III are used. In particular the ratios of 1.6 to 3.8, more specifically 1.8 to 3.3 eq, more specifically 1.9 to 2.8 eq or 1.9 to 2.5 of water per mole of compound III may be favorable according to the present invention. In one further particular embodiment, advantages can be achieved if the amounts of water used in step (i) are 0.5 to 0.95 eq or more than 1.5 eq of water to 4 eq per mole of compound III.

In step (i), KOH is used. It is preferred if at least 2 equivalents of base, more specifically at least 2.5 equivalents of base, even more specifically at least 3 equivalents of base per 1 equivalent of compound III are used. It may be preferably if at least 3.2 eq, more specifically at least 3.4 eq per 1 equivalent of compound III are used. Furthermore, it may be advantageous, if the amount of base is 2 to 6 eq, in particular 2.5 to 5.5 eq, more specifically 2.5 to 5 eq, even more specifically 3 to 5 eq per mole of compound III.

KOH is particularly used in solid form, preferably as solid pellets, flakes, micropills and/or powder.

The base, in particular solid KOH, is used such that the inventive range of water present in the reaction is kept. Then, some of the base is dissolved in the reaction solution and some is still present in solid form during the reaction.

The KOH can be added in one or more portions, for example 2 to 8 portions, to the reaction mixture. KOH can also be added in a continuous manner. Preferably, the KOH is added after compound III has been charged to the reaction vessel. However, the order may also be changed and the compound III is added to the reaction mixture already containing the KOH.

The reaction temperature when adding KOH in step (i) is preferably held at a maximum of 60° C., more specifically at a maximum of 50° C. Generally, it is also preferred to have a reaction temperature when adding KOH of at least 20° C., in particular at least room temperature, in particular at least 25° C. In a further embodiment, the temperature is at least 30° C. It may be preferred if the temperature is at least 35° C. or at least 45° C. The temperature of the reaction mixture can be for example held in these ranges by adding the KOH in portions or continuously.

The overall reaction temperature in step (i) is preferably held at a maximum of 70° C., in particular at a maximum of 60° C., more preferably at a maximum of 50° C. Generally, it is also preferred to have a reaction temperature of at least 20° C., in particular at least room temperature, in particular at least 25° C. In a further embodiment, the temperature is at least 30° C. It may be preferred if the temperature is at least 35° C.

In case a work-up of the reaction mixture after step (i) is suitable, it can be carried out by procedures known in a general manner to the person skilled in the art. It may be preferred if water is added to the reaction mixture after completion of step (i) and the resulting mixture is heated while stirring dependent on the melting point of the organic content. The temperature during this heating is held preferably from 30° C. to 70° C., more specifically 40° C. to 60° C., even more specifically 50° C. to 60° C. The organic phase may, for example, be separated and dissolved in a suitable solvent such as dimethyl formamide (DMF), N-methylpyrrolidone (NMP), dimethylsulfoxide (DMSO) or dimethylacetamide (DMAC). Dimethylsulfide, if still present, is preferably removed by distillation before or after the solvent addition. The reaction mixture may then be used directly for the next step (see below) or, if appropriate, further worked-up and/or purified by e.g. recrystallization and/or chromatography.

By means of the inventive process, the oxiranes of formula II can be prepared in high yields. Preferably, the yields are at least 60%, more preferably at least 70%, even more preferred at least 75%, even more preferred at least 80%.

One side product that may occur, if $R^1$ is iso-propyl is the following compound II''

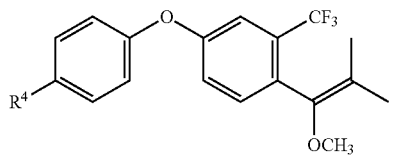

wherein $R^4$ is defined above. In particular, in formula II', $R^4$ is Cl.

The oxirane II obtained according to the inventive process (step (i)) can be further converted into a triazole of formula I. Consequently, according to a further embodiment of the invention, the process further comprises the following step:
(ii) reacting the oxirane of the formula II resulting from step (i) with 1H-1,2,4-triazole and a base, resulting in compounds of formula I,

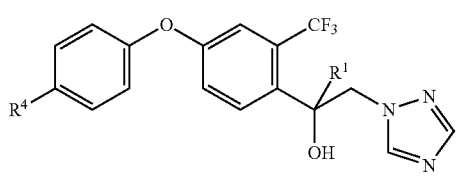

wherein the variables $R^1$ and $R^4$ are as defined and preferably defined for compounds II and III above.

One embodiment of the invention, thus, relates to a process for the preparation of compounds I,

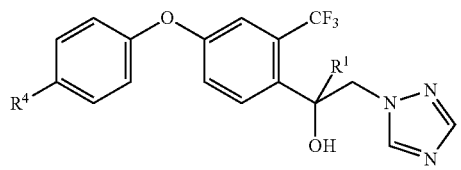

wherein the variables $R^1$ and $R^4$ are as defined and preferably defined for compounds II and III above; comprising the following steps:
(i) reacting an oxo compound of the formula III

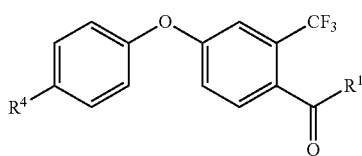

with dimethyl sulfide $(CH_3)_2S$ and dimethylsulfate $(CH_3)_2SO_4$, forming the reagent IV, trimethylsulfonium methylsulfate $[(CH_3)_3S^+ \ CH_3SO_4^-]$, in aqueous solution in the presence of potassium hydroxide (KOH), wherein dimethyl sulfide and dimethyl sulfate are used in a molar ratio of 1:1 to 2:1, and wherein at most 10 weight-% organic solvent selected from alcohols, nitrils and aromatic hydrocarbons, in relation to the amount of compound III, are added apart from the reagents used; and
(ii) reacting the reaction product resulting from step (i) with 1H-1,2,4-triazole and a base.

Compounds I are disclosed in WO 2013/007767.

In step (ii), the oxirane is reacted with 1H-1,2,4-triazole and a base.

Preferably, an inorganic base is used and said inorganic base is preferably selected from NaOH, KOH, $Na_2CO_3$ and $K_2CO_3$, more specifically from NaOH and KOH. According to one embodiment, NaOH is used. According to a further embodiment, KOH is used.

According to a further embodiment, an organic base is used in step (ii). For example 4-(dimethylamino)-pyridine (DMAP), 1,4-diazabicyclo[2.2.2]octane (DABCO), pyridine, N,N-diisopropylethylamine, tripropylamine, N,N-dimethylcyclohexylamine or morpholine. Preferred are DMAP and DABCO.

According to a specific embodiment, the sodium salt of 1H-1,2,4-triazole as a base is used, wherein said sodium salt is prepared using triazole and a base preferably selected from NaOH, NaH and Na-alcoholates. See also DE 3042302.

The amount of base used in step (ii) is preferably equal to or less than 1 eq, in particular less than 1 eq, more preferably equal to or less than 0.8 eq, even more preferably equal to or less than 0.6 equivalents per 1 equivalent of compound II. Also preferred are amounts of base being equal to or less than 0.4 equivalents, in particular equal to or less than 0.2 equivalents, specifically equal to or less than 0.1 eq per 1 equivalent of compound II. Preferably, at least 0.1 eq, more preferably at least 0.2 equivalents, in particular at least 0.3 eq base per 1 equivalent of compound II are used.

It may be preferred, if less than 1 eq of base in relation to the compound II is used. In specific embodiments thereof, NaOH is used as base, preferably in an amount as given above, in particular in an amount of 0.1 to 0.55 eq in relation to the oxirane of formula II.

In order to have preferably low reaction times, temperatures of at least 100° C., more preferably at least 110° C. It is also an embodiment to reflux the reaction mixture. Preferably, the reaction temperature is not higher than 150° C., in particular not higher than 130° C. Specifically, a reaction temperature of 110° C. to 130° C. is used.

The amount of 1H-1,2,4-triazole used in step (ii) generally is at least 1 eq per mole of oxirane II. According to one embodiment, the 1H-1,2,4-triazole is used in excess in relation to the oxirane II. Preferred are more than 1 eq to 2 eq, more preferably more than 1 eq to 1.8 eq, even more preferred more than 1 eq to 1.6 eq. Mostly for economic reason, it can be preferred to use at least 1.1 eq, specifically 1.15 eq, to 1.5 eq of triazole in relation to oxirane II.

The solvent used in step (ii) is preferably selected from dimethylformamide, dimethylacetamide, N-methylpyrrolidone and dimethylsulfoxide. Most preferred is dimethylformamide.

Generally, one further undesired side product in the synthesis of compounds I that may occur in undesired amounts is the symmetric triazole I" that is formed together with the desired triazole of formula I, leading, consequently, to lower yields of the desired product of formula I.

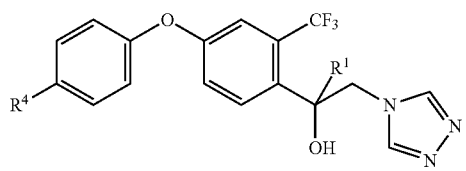

wherein $R^1$ and $R^4$ are defined and preferably defined above.

It has been found that if the reaction product I resulting from step (ii) is crystallized as described according to the invention, the product I can be obtained in high yields and purity.

Consequently, according to one preferred embodiment of the invention, the compounds I resulting from step (ii) are crystallized from a suitable solvent. This step is called final work up step (ii-1). Suitable solvents are, for example, selected from toluene, ortho-xylene, an aliphatic alcohol, acetonitrile, carbonic acid ester and cyclohexane, or any mixtures thereof, in particular from toluene, an aliphatic alcohol and carbonic acid ester and any mixture thereof.

According to the invention, it is possible to reduce the amount of I" in favor of the desired product I. Consequently, according to the inventive process, it is possible to highly improve the yield of the triazole I compared to common prior art processes.

In particular, the aliphatic alcohol is selected from methanol, ethanol, n-propanol, iso-propanol, n-butanol, isobutanol and any mixture thereof. In particular, the aliphatic alcohol is selected from methanol and ethanol and any mixture thereof.

Examples for suitable carbonic acid esters are n-butyl acetate or ethyl acetate and any mixture thereof.

Generally, for the crystallizing step, the reaction solvent, in particular dimethylformide as described above, is firstly evaporated in large part, preferably under reduced pressure. Preferably, at least 55% of the solvent, more preferably at least 60% of the solvent, more specifically at least 70% of the solvent are removed. Specifically, it may be preferred, if at least 80%, more specifically at least 90% of the solvent, such as DMF, are removed The solvent can then be recycled to be used again in the process step (ii), if necessary after it has been further rectificated before.

Then, water and the respective suitable solvent such as an ether, for example diethylether, diisopropylether, methyl-tert-butylether (MTBE), methylenechloride and/or toluene, in particular toluene, are added. Also ethyl acetate and/or n-butyl acetate can be appropriate as solvent. The product I is then preferably obtained by crystallization directly from the concentrated, e.g. toluene-reaction mixture. Also preferred and suitable according to the invention is the change of solvent to e.g. methanol or ethanol (see above) for the crystallization of the products.

According to one embodiment, seed crystals are added for the crystallization step.

By using the inventive crystallizing step according to the inventive process, in particular when carrying out the process steps (ii) the content of the undesired symmetric triazole I" can be reduced to equal or less than 10%, more preferably equal or less than 8%, even more preferably equal or less than 5%, even more preferably equal or less than 2%.

Preferably, the ratio of isolated compound I to I" is at least 20:1, more preferably at least 30:1, even more preferably 50:1, more specifically 70:1. In particular, the ratio of compound I to I" is at least 30:1.

It is in particular surprising that crystallization of a reaction product comprising compound I as described and preferably described herein from a carbonic acid esters, such as in particular n-butyl acetate or ethyl acetate or any mixture thereof, results in very high purity of the product, namely high contents of the desired product I is obtained.

Consequently, according a further aspect, the present invention relates to a process for purification of a reaction product comprising a compound of formula I, comprising the step (iia) crystallizing said reaction product from one or more carbonic acid ester(s)

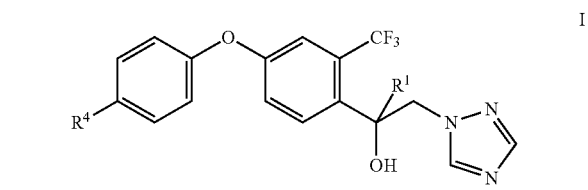

wherein $R^1$ is $C_1$-$C_6$-alkyl or $C_3$-$C_8$-cycloalkyl; and $R^4$ is F or Cl.

It has been found that if the reaction product comprising compound I is crystallized according to the invention, the product I can be obtained in high yields and purity.

Examples for suitable carbonic acid esters are n-butyl acetate or ethyl acetate and any mixture thereof.

According to one embodiment, seed crystals are added for the crystallization step.

By using the inventive crystallizing step the content of the undesired symmetric triazole I" can be reduced to equal or less than 10%, more preferably equal or less than 8%, even more preferably equal or less than 5%, even more preferably equal or less than 2%.

Preferably, the ratio of isolated compound I to I" is at least 20:1, more preferably at least 30:1, even more preferably 50:1, more specifically 70:1. In particular, the ratio of compound I to I" is at least 30:1.

Following the inventive process comprising step (i), also common methods of further reacting the oxiranes II to end products I can be carried out.

For example, the epoxide ring of compounds II may be cleaved by reaction with alcohols R²OH preferably under acidic conditions to result in compounds V:

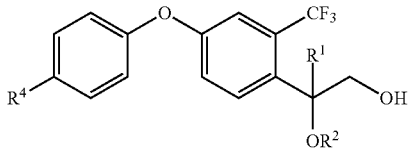

Thereafter, the resulting compounds V are reacted with halogenating agents or sulfonating agents such as PBr₃, PCl₃ mesyl chloride, tosyl chloride or thionyl chloride, to obtain compounds VI wherein LG' is a nucleophilically replaceable leaving group such as halogen, alkylsulfonyl, alkylsulfonyloxy and arylsulfonyloxy, preferably chloro, bromo or iodo, particularly preferably bromo or alkylsulfonyl. Then compounds VI are reacted with 1H-1,2,4-triazole to obtain compounds I as known in the art and/or described above:

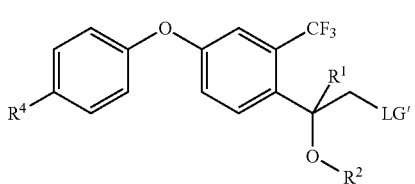

For obtaining compounds of formula I, wherein the alcohol group is derivatized (resulting in "OR²", compounds I-1, see below), the following step can be subsequently carried out:

(iii) derivatizing the compound of formula I from step (ii) under basic conditions with R²-LG, wherein LG is a nucleophilically replaceable leaving group;

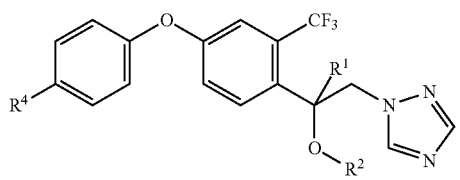

wherein the variables R¹ and R⁴ are as defined and preferably defined herein, and wherein
R² is $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl $C_1$-$C_6$ alkyl, phenyl, phenyl-$C_1$-$C_4$-alkyl, phenyl-$C_2$-$C_4$-alkenyl or phenyl-$C_2$-$C_4$-alkynyl;
wherein the aliphatic moieties of R² are not further substituted or do carry one, two, three or up to the maximum possible number of identical or different groups $R^{12a}$ which independently are selected from:
$R^{12a}$ halogen, OH, CN, nitro, $C_1$-$C_4$-alkoxy, $C_3$-$C_8$-cycloalkyl, $C_3$-$C_8$-halocycloalkyl and $C_1$-$C_4$-halogenalkoxy;

wherein the cycloalkyl and/or phenyl moieties of R² are not further substituted or do carry one, two, three, four, five or up to the maximum number of identical or different groups $R^{12b}$ which independently are selected from:
$R^{12b}$ halogen, OH, CN, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy.

LG represents a nucleophilically replaceable leaving group such as halogen, alkylsulfonyl, alkylsulfonyloxy and arylsulfonyloxy, preferably chloro, bromo or iodo, particularly preferably bromo. Preferably a base is used in step (iii) such as for example, NaH.

Suitable solvents are for example ethers, in particular cyclic ethers. Possible solvents are for example tetrahydrofuran (THF), 2-methyl-tetrahydrofuran (2-Me-THF), diethyl ether, TBME (tert-butyl methyl ether), CPME (cyclopentyl methyl ether), DME (1,2-dimethoxyethane) and 1,4-dioxane. Further solvents that may be suitable are, for example, diisopropyl ether, di-n-butyl ether and/or diglyme. Often, the use of THF or 2-methyl-THF is particularly suitable. Furthermore, it may also be suitable to use combinations of two or more different solvents, such as for example any combination of the solvents listed above or any one of the listed ethers with aliphatic hydrocarbons like n-hexane, heptane or aromatic hydrocarbons like toluene or xylenes.

The skilled person is familiar with the reaction in step (iii) and may vary the reaction conditions analogously to known syntheses.

The starting oxo-group containing compounds III for the inventive processes can be synthesized as described in the above mentioned literature and patent applications. Generally, the skilled person may obtained by various routes in analogy to prior art processes known (cf. J. Agric. Food Chem. (2009) 57, 4854-4860; EP 0 275 955 A1; DE 40 03 180 A1; EP 0 113 640 A2; EP 0 126 430 A2). In the following, synthesis routes for obtaining the precursors are given. See also PCT/EP2014/076839 for specific process conditions.

In a first process, for example, phenoles A are reacted, in a first step, with derivatives B, wherein X¹ stands for I or Br, in particular Br, preferably in the presence of a base to result in compounds C.

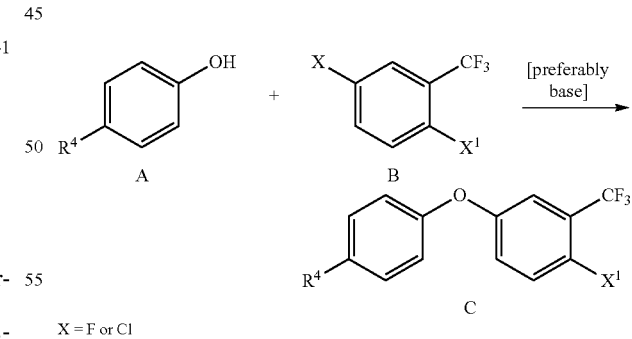

Thereafter, the resulting compounds C, in particular X¹ is Br, are then transformed into Grignard reagents by the reaction with transmetallation reagents such as isopropylmagnesium halides and subsequently reacted with acetyl chloride preferably under anhydrous conditions and preferably in the presence of a catalyst such as CuCl, CuCl₂, AlCl₃, LiCl and mixtures thereof, to obtain acetophenones D.

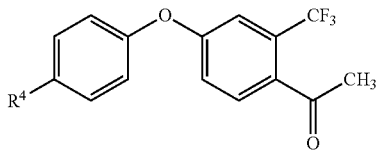

In a second process to obtain the precursors is as follows. In a first step, a halo derivative E, wherein $X^2$ is halogen, in particular F, and $X^3$ is halogen, in particular Br, is reacted with a transmetallation agent such as e.g. isopropylmagnesium bromide followed by an acyl chloride agent $R^1COCl$ (e.g. acetyl chloride) preferably under anhydrous conditions and optionally in the presence of a catalyst such as CuCl, $CuCl_2$, $AlCl_3$, LiCl and mixtures thereof, to obtain ketones F.

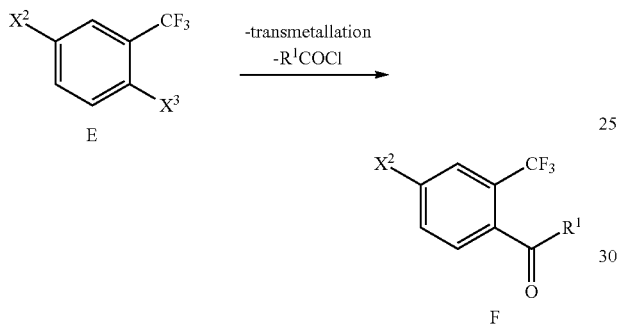

Thereafter, ketones F are reacted with phenoles A preferably in the presence of a base to obtain compounds III wherein $R^1$ is as defined and preferably defined, respectively, herein.

Compounds III may also be obtained in analogy to the first process described for compounds D (preferred conditions for the process step, see above). This is illustrated in the following:

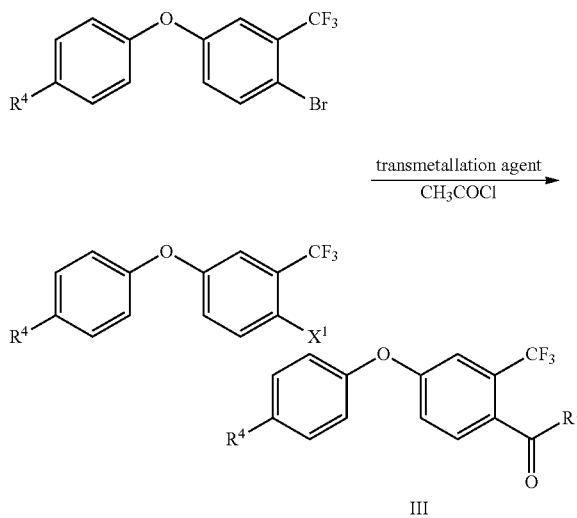

The ketones III may specifically be obtained by the following steps:

(a) reacting a compound of the formula (E)

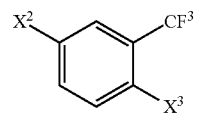

wherein $X^2$ is halogen, in particular Cl or F, more specifically F, and $X^3$ is halogen, in particular Br, with R'—Mg-Hal or Mg and $R^1C(\!=\!O)Cl$ in the presence of a Cu(I)-catalyst in an amount of 0.005 to 0.065 mole equivalents per 1 mole of compound (E), to result in compounds (F)

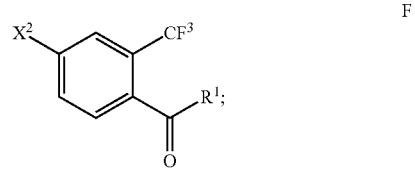

and
(b) reacting compound (F) as defined in step (a) with a phenol derivative of formula (A')

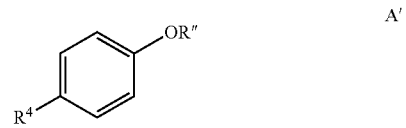

in the presence of a base if R'' is hydrogen;
wherein the variables are defined as follows:
$R^4$ is F or Cl;
R' is $C_1$-$C_4$-alkyl or $C_3$-$C_6$-cycloalkyl; and
R'' is hydrogen or an alkali metal kation.

According to a preferred embodiment, the Grignard reagent R'—Mg-Hal is used in the process. R' in the Grignard reagent is $C_1$-$C_4$-alkyl or $C_3$-$C_6$-cycloalkyl, in particular is selected from methyl, ethyl, isopropyl, tert-butyl, sec-butyl and cyclopropyl. Specifically, R' in the Grignard reagent is selected from isopropyl, tert-butyl, sec-butyl and cyclopropyl. In one specific embodiment, R' is isopropyl. In one further embodiment, R' is sec-butyl. Hal stands for halogen, in particular Cl or Br. Also more than one Grignard reagent can be used in the same reaction, such as, for example the reagent, wherein Hal is Br together with the respective reagent (having the same R'), wherein Hal is Cl. According to one embodiment, Hal is Cl and R' in the Grignard reagent is selected from isopropyl, tert-butyl, sec-butyl and cyclopropyl. According to a further embodiment, Hal is Br and R' in the Grignard reagent is selected from isopropyl, tert-butyl, sec-butyl and cyclopropyl. In one preferred embodiment, in the inventive process, the Grignard reagent is (iso-propyl)-Mg—Cl or (iso-propyl)-Mg—Br. In one further preferred embodiment, in the inventive process, the Grignard reagent is (sec-butyl)-Mg—Cl or (sec-butyl)-Mg—Br.

Preferably, the Grignard reagent is used in an amount of 1 eq to 2 eq, in particular 1.1 to 1.8 eq, more specifically 1.2 to 1.6 eq, in relation to one equivalent of compound (E). In particular the amounts of 1.3 to 1.5, more particularly 1.2 to 1.4 per mole of compound (E) may be favorable according to the present invention. Usually, the Grignard reagent is used in excess, preferably in slight excess.

In the carbonyl chloride $R^1C(=O)Cl$, $R^1$ is $C_1$-$C_6$-alkyl or $C_3$-$C_8$-cycloalkyl, in particular selected from $CH_3$, $CH(CH_3)_2$ and cyclopropyl.

The carbonyl chloride $R^1C(=O)Cl$ is preferably used in an equimolar amount or in excess compared to the reagent of formula (E). Specifically, the carbonyl chloride is used in an amount of 1 eq to 3 eq, in particular 1.1 to 2.5 eq, more specifically 1.2 to 2 eq, in relation to one equivalent of compound (E). In particular the amounts of 1.3 to 1.8 eq, more specifically 1.4 to 1.6 eq per mole of compound (E) may be favorable according to the present invention. Usually, the carbonyl chloride is used in excess, preferably in slight excess.

The Grignard reagent is added in the manner as is common to the skilled person. In particular, it can be added as solution in an appropriate solvent such as tetrahydrofurane (THF), 1,4-dioxane, diethylether and 2-methyl-tetrahydrofurane.

Examples for appropriate solvents for step (a) are aprotic organic solvents such as for example diethylether, tetrahydrofurane (THF), methyl-tert-butylether (MTBE), toluene, ortho-xylene, meta-xylene, para-xylene and mixtures thereof.

The reaction temperature when adding the Grignard reagent is preferably held at a maximum of 50° C., in particular at a maximum of 40° C., more preferably at a maximum of 35° C. Generally, it is preferred to have a reaction temperature of 20° C. to 45° C., in particular room temperature to 45° C., in particular 25° C. to 40° C. In a further embodiment, the temperature is 20° C. to 35° C., specifically 25° C. to 30° C.

An appropriate Cu(I)-catalyst for the inventive process is a Cu(I) salt or Cu(I) oxide, in particular a Cu(I) salt such as Cu(I)Cl or Cu(I)Br or any mixture thereof. According to one specific embodiment, Cu(I)Cl is used. In this embodiment, the Cu(I)-catalyst is present in an amount of 0.005 to 0.065 mol equivalents per 1 mole of compound (E). It may be preferred if 0.005 to 0.055 mol equivalents per 1 mole of compound (E) are used. Also, it may be preferred if 0.055 to 0.045 mol equivalents per 1 mole of compound (E), more specifically 0.005 to 0.04 mol equivalents per 1 mole of compound (E) are used. In particular, the amount of Cu(I)-catalyst is 0.01 to 0.03 mole equivalents per 1 mole of compound (E), more particularly 0.015 to 0.025 mole equivalents, even more particularly 0.015 to 0.02, per 1 mole of compound (E), specifically 0.018 to 0.023 mole equivalents per 1 mole of compound (E). According to one embodiment, the Cu(I)-catalyst is added in several portions to the reaction mixture, for example in two portions a half of the total amount.

Examples for appropriate solvents for step (b) are aprotic organic solvents such as for example dimethyl formamide (DMF), N-methyl pyrrolidone (NMP), Dimethyl imidazolidinone (DMI), toluene, o-xylene, dimethylacetamide (DMA) and any mixtures thereof. In particular DMF, NMP, toluene and DMA or any mixtures, more specifically DMF, are particularly suitable.

The base used in step (b) is preferably an inorganic base, according to one embodiment selected from NaOH, KOH, $Na_2CO_3$ and $K_2CO_3$, more specifically from $Na_2CO_3$ and $K_2CO_3$. According to one particular embodiment, $Na_2CO_3$ is used. According to a further particular embodiment, $K_2CO_3$ is used.

The base can be used in solid form or as a solution, e.g. as aqueous solution.

The reagents for step (b) are preferably added at ambient temperature and the reaction temperature is then elevated, wherein the reaction temperature after the reagents have been added is preferably held at a maximum of 150° C., in particular at a maximum of 140° C., more preferably at a maximum of 130° C. Generally, it is preferred to have a reaction temperature of 20° C. to 135° C., in particular 50° C. to 135° C., more particularly 100° C. to 130° C.

See PCT/EP2014/076839 for details on conditions.

The starting compounds (E) can be synthesized as known to the skilled person or are also partly commercially available.

If individual compounds cannot be directly obtained by the routes described above, they can be prepared by derivatization of other compounds.

In case a work-up of the reaction mixture in any of the reaction steps of the inventive process or the other processes described, is suitable, it can be carried out by procedures known in a general manner to the person skilled in the art. Usually, the reaction mixture is extracted with a suitable organic solvent (for example aromatic hydrocarbons such as toluene and xylenes) and the residue is, if appropriate, purified by recrystallization and/or chromatography.

In the definitions of the variables given herein, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_6$-alkyl" refers to a straight-chained or branched saturated hydrocarbon group having 1 to 6 carbon atoms, e.g. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Likewise, the term "$C_2$-$C_4$-alkyl" refers to a straight-chained or branched alkyl group having 2 to 4 carbon atoms, such as ethyl, propyl (n-propyl), 1-methylethyl (iso-propoyl), butyl, 1-methylpropyl (sec.-butyl), 2-methylpropyl (iso-butyl), 1,1-dimethylethyl (tert.-butyl).

The term "$C_1$-$C_6$-haloalkyl" refers to an alkyl group having 1 or 6 carbon atoms as defined above, wherein some or all of the hydrogen atoms in these groups may be replaced by halogen atoms as mentioned above. Examples are "$C_1$-$C_2$-haloalkyl" groups such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl.

The term "$C_2$-$C_6$-alkenyl" refers to a straight-chain or branched unsaturated hydrocarbon radical having 2 to 6 carbon atoms and a double bond in any position. Examples are "$C_2$-$C_4$-alkenyl" groups, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond. Examples are "$C_2$-$C_4$-alkynyl" groups, such as ethynyl, prop-1-ynyl, prop-2-ynyl (propargyl), but-1-ynyl, but-2-ynyl, but-3-ynyl, 1-methyl-prop-2-ynyl.

The term "$C_3$-$C_8$-cycloalkyl" refers to monocyclic saturated hydrocarbon radicals having 3 to 8 carbon ring members, such as cyclopropyl, cyclobutyl, cyclopentyl, cyclohexyl, cycloheptyl or cyclooctyl.

The term "$C_3$-$C_8$-cycloalkyl-$C_1$-$C_4$-alkyl" refers to alkyl having 1 to 4 carbon atoms (as defined above), wherein one hydrogen atom of the alkyl radical is replaced by a cycloalkyl radical having 3 to 8 carbon atoms (as defined above).

The term "$C_1$-$C_6$-alkoxy" refers to a straight-chain or branched alkyl group having 1 to 6 carbon atoms which is bonded via an oxygen, at any position in the alkyl group. Examples are "$C_1$-$C_4$-alkoxy" groups, such as methoxy, ethoxy, n-propoxy, 1-methylethoxy, butoxy, 1-methylpropoxy, 2-methylpropoxy or 1,1-dimethylethoxy.

The term "$C_1$-$C_6$-haloalkoxy" refers to a $C_1$-$C_6$-alkoxy radical as defined above, wherein some or all of the hydrogen atoms in these groups may be replaced by halogen atoms as mentioned above. Examples are "$C_1$-$C_4$-haloalkoxy" groups, such as $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloro-ethoxy, $OC_2F_5$, 2-fluoropropoxy, 3-fluoropropoxy, 2,2-difluoropropoxy, 2,3-difluoropropoxy, 2 chloropropoxy, 3-chloropropoxy, 2,3-dichloropropoxy, 2-bromo-propoxy, 3 bromopropoxy, 3,3,3-trifluoropropoxy, 3,3,3-trichloropropoxy, $OCH_2$—$C_2F_5$, $OCF_2$—$C_2F_5$, 1-fluoromethyl-2-fluoroethoxy, 1-chloromethyl-2-chloroethoxy, 1-bromomethyl-2-bromoethoxy, 4-fluorobutoxy, 4-chlorobutoxy, 4-bromobutoxy or nonafluorobutoxy.

The term "phenyl-$C_1$-$C_6$-alkyl" refers to alkyl having 1 to 6 carbon atoms (as defined above), wherein one hydrogen atom of the alkyl radical is replaced by a phenyl radical. Likewise, the terms "phenyl-$C_2$-$C_6$-alkenyl" and "phenyl-$C_2$-$C_6$-alkynyl" refer to alkenyl and alkynyl, respectively, wherein one hydrogen atom of the aforementioned radicals is replaced by a phenyl radical.

The meanings and preferred meanings described in the following for the variables $R^1$, $R^2$, and $R^4$ apply to compounds and the precursors of the compounds I and side products in any of the above detailed inventive processes.

$R^2$ in compounds I-1 prepared according to the present invention or in precursors thereof, is as defined above. Particularly preferred embodiments of $R^2$ according to the invention are in Table P2 below, wherein each line of lines P2-1 to P2-87 corresponds to one particular embodiment of the invention, wherein P2-1 to P2-87 are also in any combination a preferred embodiment of the present invention.

TABLE P2

| line | $R^2$ |
|---|---|
| P2-1 | $CH_3$ |
| P2-2 | $CH_2CH_3$ |
| P2-3 | $CH(CH_3)_2$ |
| P2-4 | $CH_2CH_2CH_3$ |
| P2-5 | $CH_2CH_2CH_2CH_3$ |
| P2-6 | $CH_2CH(CH_3)_2$ |
| P2-7 | $CF_3$. |
| P2-8 | $CHF_2$ |
| P2-9 | $CFH_2$ |
| P2-10 | $CCl_3$. |
| P2-11 | $CHCl_2$ |
| P2-12 | $CClH_2$ |
| P2-13 | $CH_2CF_3$ |
| P2-14 | $CH_2CHF_2$ |
| P2-15 | $CH_2CCl_3$ |
| P2-16 | $CH_2CHCl_2$ |
| P2-17 | $CH_2CH_2OCH_2CH_3$ |
| P2-18 | $CH(CH_3)OCH_2CH_3$ |
| P2-19 | $CH(CH_3)OCH_3$ |
| P2-20 | $CH_2OCH_3$ |
| P2-21 | $CH_2CH_2OCH_3$ |
| P2-22 | $CH_2OCF_3$ |
| P2-23 | $CH_2CH_2OCF_3$ |
| P2-24 | $CH_2OCCl_3$ |
| P2-25 | $CH_2CH_2OCCl_3$ |
| P2-26 | $CH_2CH_2OH$ |
| P2-27 | $CH_2OH$ |
| P2-28 | $CH_2CH_2CH_2OH$, |
| P2-29 | $CH(CH_3)CH_2OH$ |
| P2-30 | $CH_2CH(CH_3)OH$ |
| P2-31 | $CH_2CH_2CH_2CH_2OH$ |
| P2-32 | $CH_2CN$ |
| P2-33 | $CH_2CH_2CN$, |
| P2-34 | $CH_2CH_2CH_2CN$, |
| P2-35 | $CH(CH_3)CH_2CN$, |
| P2-36 | $CH_2CH(CH_3)CN$, |
| P2-37 | $CH_2CH_2CH_2CH_2CN$ |
| P2-38 | $CH=CH_2$ |
| P2-39 | $C(CH_3)=CH_2$ |
| P2-40 | $CH=CHCH_3$ |
| P2-41 | $CH_2CH=CH_2$ |
| P2-42 | $CH_2CH=CHCH_3$ |
| P2-43 | $CH_2C(CH_3)=CH_2$ |
| P2-44 | $C(CH_3)=CH(CH_3)$ |
| P2-45 | $C(CH_3)=C(CH_3)2$ |
| P2-46 | $CH=C(CH_3)_2$ |
| P2-47 | $CH=C(Cl)_2$ |
| P2-48 | $C(CH_3)=CH_2$ |
| P2-49 | $CH_2C(Cl)=CH_2$ |
| P2-50 | $CH_2C(H)=CHCl$ |
| P2-51 | $CH=CHCH_2OH$ |
| P2-52 | $CH=C(CH_3)OH$ |
| P2-53 | $CH=CHOCH_3$ |
| P2-54 | $CH=CHCH_2OCH_3$ |
| P2-55 | $CH_2CH=CHCH_2OCH_3$ |
| P2-56 | $CH=CHOCF_3$ |
| P2-57 | $CH=CHCH_2OCF_3$ |
| P2-58 | $CH=CHOCCl_3$ |
| P2-59 | $CH=CHCH_2OCCl_3$ |
| P2-60 | $CH_2CH=CH(C_3H_5)$ |
| P2-61 | $CH_2CH=CH(C_4H_7)$ |
| P2-62 | $CH_2CH=CH(1-Cl-C_3H_4)$ |
| P2-63 | $CH_2CH=CH(1-F-C_3H_4)$ |
| P2-64 | $C=CH$ |
| P2-65 | $CH_2C=CH$ |
| P2-66 | $CH_2C=CCH_3$ |
| P2-67 | $CH_2C=CCH_2CH_3$ |
| P2-68 | $CH_2C=CCl$ |
| P2-69 | $CH_2C=CF$ |
| P2-70 | $CH_2C=C$—$I$ |
| P2-71 | $CH_2C=CCH_2OH$ |
| P2-72 | $C=COCH_3$ |
| P2-73 | $CH_2C=COCH_3$ |
| P2-74 | $CH_2C=CCH_2OCH_3$ |
| P2-75 | $C=COCF_3$ |
| P2-76 | $CH_2C=COCF_3$ |
| P2-77 | $C=COCCl_3$ |
| P2-78 | $CH_2C=COCCl_3$ |
| P2-79 | $CH_2$-(cyclopropyl) |
| P2-80 | $CH_2$-(cyclobutyl) |
| P2-81 | $CH_2$-(1-Cl-cyclopropyl) |
| P2-82 | $CH_2$-(1-F-cyclopropyl) |

TABLE P2-continued

| line | R² |
|---|---|
| P2-83 | CH₂C₆H₅ |
| P2-84 | CH₂-(4-Cl)—C₆H₄ |
| P2-85 | CH₂-(4-F)—C₆H₄ |
| P2-86 | CH₂-(4-CH₃)—C₆H₄ |
| P2-87 | CH₂-(4-OCH₃)—C₆H₄ |

Specifically, the following compounds IC.1 to IC.8 can advantageously be prepared using the process according to the present invention:

Compound IC.1 2-[4-(4-chlorophenoxy)-2-(trifluoromethyl)phenyl]-1-(1,2,4-triazol-1-yl)propan-2-ol; (R¹=methyl, R⁴=Cl, R²=H)

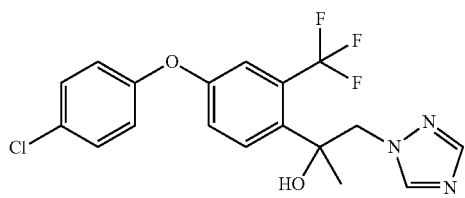 [SMILES: CC(O)(Cn1cncn1)c1ccc(Oc2ccc(Cl)cc2)cc1C(F)(F)F]

Compound IC.2 1-[4-(4-chlorophenoxy)-2-(trifluoromethyl)phenyl]-1-cyclopropyl-2-(1,2,4-triazol-1-yl)ethanol; (R¹=cyclopropyl, R⁴=Cl, R²=H)

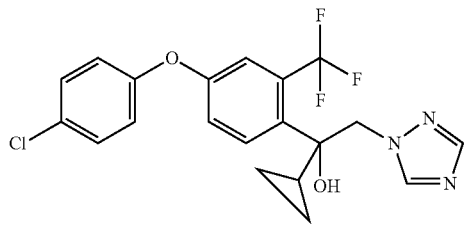 [SMILES: OC(Cn1cncn1)(c1ccc(Oc2ccc(Cl)cc2)cc1C(F)(F)F)C1CC1]

Compound IC.3 2-[4-(4-chlorophenoxy)-2-(trifluoromethyl)phenyl]-3-methyl-1-(1,2,4-triazol-1-yl)butan-2-ol; (R¹=i-propyl, R⁴=Cl, R²=H)

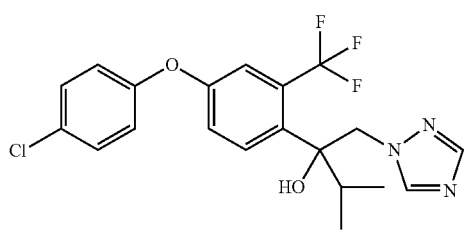 [SMILES: CC(C)C(O)(Cn1cncn1)c1ccc(Oc2ccc(Cl)cc2)cc1C(F)(F)F]

Compound IC.4 2-[4-(4-chlorophenoxy)-2-(trifluoromethyl)phenyl]-1-(1,2,4-triazol-1-yl)butan-2-ol; (R¹=ethyl, R⁴=Cl, R²=H)

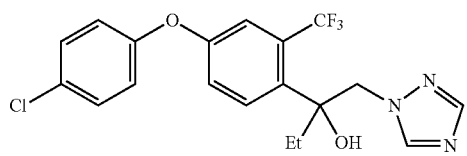 [SMILES: CCC(O)(Cn1cncn1)c1ccc(Oc2ccc(Cl)cc2)cc1C(F)(F)F]

Compound IC.5 1-[2-[4-(4-chlorophenoxy)-2-(trifluoromethyl)phenyl]-2-methoxy-propyl]-1,2,4-triazole; (R¹=methyl, R⁴=Cl, R²=CH₃)

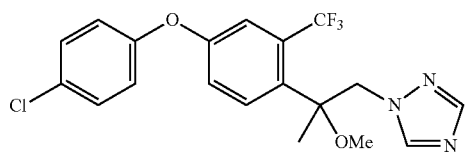 [SMILES: COC(C)(Cn1cncn1)c1ccc(Oc2ccc(Cl)cc2)cc1C(F)(F)F]

Compound IC.6 1-[2-[4-(4-chlorophenoxy)-2-(trifluoromethyl)phenyl]-2-cyclopropyl-2-methoxyethyl]-1,2,4-triazole; (R¹=cyclopropyl, R⁴=Cl, R²=CH₃)

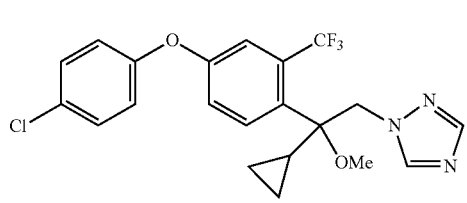 [SMILES: COC(Cn1cncn1)(c1ccc(Oc2ccc(Cl)cc2)cc1C(F)(F)F)C1CC1]

Compound IC.7 1-[2-[4-(4-chlorophenoxy)-2-(trifluoromethyl)phenyl]-2-methoxy-butyl]1,2,4-triazole; (R¹=ethyl, R⁴=Cl, R²=CH₃)

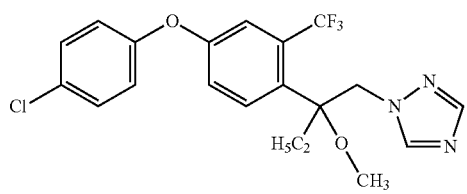

Compound IC.8 2-[4-(4-fluorophenoxy)-2-(trifluoromethyl)phenyl]-1-(1,2,4-triazol-1-yl)propan-2-ol; ($R^1$=methyl, $R^4$=F, $R^2$=H)

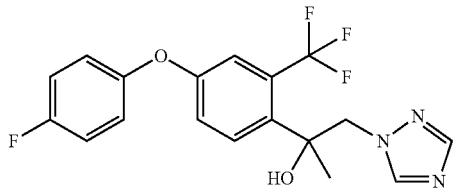 [SMILES: CC(O)(Cn1cncn1)c1ccc(Oc2ccc(F)cc2)cc1C(F)(F)F]

See also WO 2013/007767.

Compounds I comprise chiral centers and they are generally obtained in the form of racemates. The R- and S-enantiomers of the compounds can be separated and isolated in pure form with methods known by the skilled person, e.g. by using chiral HPLC. Furthermore, compounds I can be present in different crystal modifications, which may differ in biological activity.

Furthermore, using the inventive crystallization step, solvates may occur, in particular from any one of compounds IC.1 to IC.8 that are likewise comprised by the present invention. A further aspect of the invention is, therefore, a crystalline solvate of compound I, in particular a crystalline solvate with a compound I selected from IC.1, IC.2, IC.3, IC.4, IC.5, IC.6, IC.7 and IC.8.

The process of the present invention allows to prepare a specific crystalline form of 2-[4-(4-chlorophenoxy)-2-(trifluoromethyl)phenyl]-3-methyl-1-(1,2,4-triazol-1-yl)butan-2-ole (compound IC.3), hereinafter also termed form A of compound IC.3, which has beneficial properties. See also PCT/EP2013/077083.

IC.3 is known from WO 2013/007767.

Form A of compound IC.3 can be characterized by its X-ray powder diffractogram at 25° C. using Cu-K$_\alpha$ radiation. Said X-ray powder diffractogram shows at least six, in particular at least 8, more particularly at least 10 or 12 and especially all of the fourteen following peak positions, given in the following table 1a as 2θ values and d-spacings:

TABLE 1a

Relevant reflections in the XRPD pattern of compound IC.3 form A

| 2θ values [°] | d [Å] |
|---|---|
| 6.26 ± 0.2 | 14.11 |
| 11.68 ± 0.2 | 7.58 |
| 12.52 ± 0.2 | 7.07 |
| 13.64 ± 0.2 | 6.49 |
| 14.69 ± 0.2 | 6.03 |
| 18.84 ± 0.2 | 4.71 |
| 19.36 ± 0.2 | 4.59 |
| 20.44 ± 0.2 | 4.35 |
| 21.32 ± 0.2 | 4.17 |
| 22.02 ± 0.2 | 4.04 |
| 22.99 ± 0.2 | 3.87 |
| 24.18 ± 0.2 | 3.68 |
| 25.22 ± 0.2 | 3.53 |
| 25.68 ± 0.2 | 3.47 |

The crystal form A of compound IC.3 is easy to handle since during production form A is obtained in the form of discrete crystals or crystallites having increased particle size. Increased particle size and the compact habit of form A facilitates filtration from mother liquour and allows easier drying of the solid material. Pure form A of IC.3 is likely to display increased stability with regard to conversion into another modification. The stability of formulations which contain the compound IC.3 in form A is likely higher than the stability of formulations which contain mixtures of different modifications of compound IC.3. The terms "pure form A" should be understood to mean that the proportion of the modification in question, based on the total quantity of compound IC.3, is at least 80% by weight in particular at least 90% by weight and especially at least 95% by weight. Furthermore, form A of compound IC.3 may show one or more of the following favorable properties: solubility, vapor pressure, dissolution rate, stability against a phase change into a different modification, stability during grinding, suspension stability, optical and mechanical properties, hygroscopicity, crystal form and size, filterability, density, melting point, stability to decomposition, color and even chemical reactivity or biological activity.

Studies on single crystals of form A demonstrate that the underlying crystal structure is monoclinic. The unit cell has the space group P2$_1$/n. The characteristic data of the crystal structure of form A (determined at 100 K, Cu-K$_\alpha$ radiation) are compiled in the following table 1b.

TABLE 1b

Crystallographic characteristics of form A of compound IC.3

| Parameter | Form A |
|---|---|
| class | Monoclinic |
| space group | P2$_1$/n |
| a | 8.0285 (2) Å |
| b | 27.8467 (6) Å |
| c | 9.1925 (2) Å |
| α | 90° |
| β | 103.3169 (10)° |
| γ | 90° |
| volume | 1991.32 (8) Å$^3$ |
| Z | 4 |
| R factor | 2.80% | a, b, c = unit cell length
α, β, γ = unit cell angle
Z = number of molecules in the unit cell Form A of compound IC.3 displays a thermogram with a characteristic melting peak in the range from 109 to 116° C. The melting point, determined as the onset of the melting peak, typically lies in the range from about 114° C. to 115° C. The values quoted here relate to values determined by differential calorimetry (differential scanning calorimetry: DSC, crimped but vented aluminium pans, heating rate 10 K/min, vented with nitrogen 150 ml/min).

Form A of compound IC.3 was prepared by example M3 as described hereinafter, followed by crystallization from a solution of compound IC.3 in lower alkanol, such as methanol. Preferably, crystallization is achieved by cooling a hot solution of compound IC.3 in the alkanol. Preferably, the hot solution has a temperature of at least 50°, e.g. from 50 to 70° C. Preferably cooling is performed with controlled cooling rate, the cooling rate being in particular from 1 to 20 k/h, in particular from 2 to 10 k/h. Single crystals of form A of compound IC.3 were obtained by diffusion of heptane into a solution of compound IC.3 in 2-propanol.

The crystallization of form A can be promoted or accelerated by seeding with seed crystals of form A of compound IC.3, for example by adding seed crystals of form A before or during the crystallization. If seed crystals are added during the crystallization, the quantity thereof is typically 0.001 to 10 wt. %, often 0.005 to 5 wt. %, in particular 0.01 to 1 wt. % and especially 0.05 to 0.5 wt. %, based on the total amount of compound IC.3 to be crystallized.

Form A of compound IC.3 is suitable as fungicide, i.e. for controlling harmful fungi, in particular for controlling plant pathogenic fungi.

Further forms of compound IC.3 have been found, namely forms B, C and D. They represent separate aspects of the present invention.

Form B of IC.3 can be obtained by crash cooling from aromatic solvents (e.g. toluene or p-xylene).

TABLE 2a

Relevant reflections in the XRPD pattern of IC.3 form B

| 2θ values [°] | d [Å] |
|---|---|
| 5.47 ± 0.2 | 16.15 |
| 5.80 ± 0.2 | 15.23 |
| 8.74 ± 0.2 | 10.11 |
| 11.05 ± 0.2 | 8.01 |
| 14.68 ± 0.2 | 6.03 |
| 16.63 ± 0.2 | 5.33 |
| 22.27 ± 0.2 | 3.99 |
| 23.65 ± 0.2 | 3.76 |
| 26.66 ± 0.2 | 3.34 |
| 26.98 ± 0.2 | 3.30 |
| 27.70 ± 0.2 | 3.22 |
| 27.96 ± 0.2 | 3.19 |

Form C can be obtained by evaporation of solutions of IC.3 from various solvents, very often together with form A. Single crystals are obtained from evaporation experiment with DMF.

TABLE 3a

Relevant reflections in the XRPD pattern of IC.3 form C

| 2θ values [°] | d [Å] |
|---|---|
| 13.03 ± 0.2 | 6.79 |
| 13.73 ± 0.2 | 6.45 |
| 14.23 ± 0.2 | 6.23 |
| 15.04 ± 0.2 | 5.89 |
| 16.10 ± 0.2 | 5.51 |
| 17.52 ± 0.2 | 5.06 |
| 17.86 ± 0.2 | 4.97 |
| 18.14 ± 0.2 | 4.89 |
| 18.85 ± 0.2 | 4.71 |
| 20.39 ± 0.2 | 4.36 |
| 20.72 ± 0.2 | 4.29 |
| 22.79 ± 0.2 | 3.90 |
| 25.29 ± 0.2 | 3.52 |

TABLE 3b

Crystallographic data of IC.3 form C Parameter

| crystal system | triclinic |
|---|---|
| space group | P$\bar{1}$ |
| a | 7.0177 (17) Å |
| b | 14.454 (4) Å |
| c | 20.482 (5) Å |
| α | 70.207 (14)° |
| β | 85.473 (14)° |
| γ | 89.391 (16)° |
| volume | 1948.5 (9) Å$^3$ |
| Z | 4 |
| R factor | 20.9% | a, b, c=length of the edges of the unit cell
α, β, γ=angles of the unit cell
Z=number of molecules in the unit cell Form D can be obtained by evaporation of a solution of IC.3 in DMSO.

TABLE 4a

Relevant reflections in the XRPD pattern of IC.3 form D

| 2θ values [°] | d [Å] |
|---|---|
| 6.10 ± 0.2 | 14.48 |
| 7.93 ± 0.2 | 11.16 |
| 11.03 ± 0.2 | 8.02 |
| 12.16 ± 0.2 | 7.28 |
| 15.69 ± 0.2 | 5.65 |
| 15.95 ± 0.2 | 5.56 |
| 17.60 ± 0.2 | 5.04 |
| 18.26 ± 0.2 | 4.86 |
| 19.10 ± 0.2 | 4.65 |
| 21.49 ± 0.2 | 4.14 |
| 23.49 ± 0.2 | 3.79 |
| 23.89 ± 0.2 | 3.73 |
| 24.27 ± 0.2 | 3.67 |
| 25.22 ± 0.2 | 3.53 |
| 26.01 ± 0.2 | 3.43 |
| 26.68 ± 0.2 | 3.34 |

The forms A, B, C and D of IC.3 are suitable as fungicides, i.e. for controlling harmful fungi, in particular for controlling plant pathogenic fungi. They may show advantages regarding its handling and formulation properties. Hence, the invention relates to the use of form(s) A, B, C and/or D of compounds IC.3 for controlling harmful fungi, in particular for controlling plant pathogenic fungi.

The invention thus also relates to agrochemical compositions containing the crystalline form(s) A, B, C and/or D of compound IC.3, and also one or more auxiliaries, conventionally used for the formulation of plant protection agents, in particular plant protection agents in the form of aqueous suspension concentrates (so-called SC's) or non-aqueous suspension concentrates (so-called OD's), and plant protection agents in the form of powders (so-called WP's) and granules (so-called WG's) dispersible in water.

The invention also relates to a method for controlling harmful fungi, in particular for controlling plant pathogenic fungi, which method comprises treating the fungi or the plants, the soil, seeds or non-living materials with the crystalline form(s) A, B, C and/or D of compound IC.3, preferably as a suitable active substance preparation, is used on plants, their habitat and/or on seeds.

They may be used for combating a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

They are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called *Stevia*); natural rubber plants or ornamental and forestry plants, such as flowers, shrubs, broad-leaved trees or evergreens, e. g. conifers; and on the plant propagation material, such as seeds, and the crop material of these plants.

They may also be used for protecting plant propagation material against infection with phyto-pathogenic fungi. The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

They may also be used for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials.

Further, said crystalline forms of compound IC.3 and the agrochemical compositions which contain the same can also be used in crops which through breeding including genetic engineering methods are tolerant towards insect or fungal attack. Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Said forms of compound IC.3 and compositions thereof, respectively, may be used for improving the health of a plant. The invention also relates to a method for improving plant health by treating a plant, its propagation material and/or the locus where the plant is growing or is to grow with an effective amount of said crystalline forms of IC.3 and compositions thereof, respectively. The term "plant health" is to be understood to denote a condition of the plant and/or its products which is determined by several indicators alone or in combination with each other such as yield (e. g. increased biomass and/or increased content of valuable ingredients), plant vigor (e. g. improved plant growth and/or greener leaves ("greening effect")), quality (e. g. improved content or composition of certain ingredients) and tolerance to abiotic and/or biotic stress. The above identified indicators for the health condition of a plant may be interdependent or may result from each other.

Said forms of compound IC.3 are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi. Plant propagation materials may be treated with said crystalline form(s) of compound IC.3 as such or a composition comprising said form(s) of compound IC.3 prophylactically either at or before planting or transplanting.

The crystalline forms of compound IC.3 and the agrochemical compositions which contain the same, can, for example, be used in the form of directly sprayable aqueous solutions, powders, suspensions and also high concentration aqueous, oily or other suspensions, oil suspensions, pastes, dusting agents, scattering agents or granules by spraying, misting, dusting, scattering or pouring. The use forms are determined by the use purposes; in each case, they should ensure the finest possible distribution of the active substances according to the invention.

The invention also relates to agrochemical compositions comprising an auxiliary and form(s) A, B, C and/or D of compounds IC.3.

The agrochemical compositions according to the invention contain any one of forms A, B, C and D of compound IC.3. The purity, based on the modification in question, is preferably at least 80 wt. %, in particular at least 90% or at least 95%, based on the total amount of compound IC.3. However, the purity, based on the modification in question, may also be as low as 5% or at least 10%, based on the total amount of compound IC.3.

The agrochemical compositions according to the invention also contain one or more auxiliaries, which are usual for the formulation of plant protection agents. In such agrochemical compositions, the quantity of active substance, i.e. the total quantity of compound IC.3 and of other active substances, if present, normally lies in the range from 1 to 98 wt. %, in particular in the range from 5 to 95 wt. %, based on the total weight of the agrochemical compositions, the remainder being one or more auxiliaries.

Suitable auxiliaries are liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

All solid and liquid substances which are normally used as carriers in plant protection agents, in particular in herbicide formulations are possible as carriers.

Solid carriers are for example mineral earths such as silicic acids, silica gels, silicates, talc, kaolin, limestone, lime, chalk, bole, loess, clay, dolomite, diatomaceous earth, calcium and magnesium sulfate, magnesium oxide, ground plastics, fertilizers such as ammonium sulfate, ammonium phosphate, ammonium nitrate, ureas and plant products such as cereal flour, tree bark, wood and nutshell flour, cellulose powder and other solid carriers.

Liquid carriers, as well as water, are also organic liquids, for example mineral oil fractions of medium to high boiling point such as kerosene and diesel oil, also coal tar oils and oils of plant or animal origin, aliphatic, cyclic and aromatic hydrocarbons, for example paraffins, tetrahydronaphthalene, alkylated naphthalenes and derivatives thereof, alkylated benzenes and derivatives thereof, including aromatic and non-aromatic hydrocarbon mixtures, for example the products marketed under the trade names Exxsol and Solvesso, alcohols such as propanol, butanol and cyclohexanol.

Typical further auxiliaries include surface-active substances, in particular those wetting agents, emulsifiers and dispersant (additives) normally used in plant protection agents, and also viscosity-modifying additives (thickeners and rheology modifiers), antifoaming agents, antifreeze agents, pH adjusting agents, stabilizers, anticaking agents and biocides (preservatives).

Possible surface-active substances are preferably anionic and nonionic surfactants. Protective colloids are also suitable surface-active substances.

The quantity of surface-active substances will as a rule be 0.1 to 50 wt. %, in particular 0.5 to 30 wt. %, based on the total weight of the plant protection agents according to the invention, or 0.5 to 100 wt. %, based on the total quantity of solid active substances in the formulation. Preferably, the surface-active substance include at least one anionic surface-active substance and at least one nonionic surface-active substance, and the proportion of anionic to nonionic surface-active substance typically lies in the range from 10:1 to 1:10.

Surface-active compounds, also termed surfactants may be anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Examples of anionic surfactants include alkyl aryl-sulfonates, aromatic sulfonates, for example ligninsulfonates (Borresperse types, Borregaard), phenylsulfonates, naphthalenesulfonates (Morwet types, Akzo Nobel), dibutylnaphthalenesulfonates (Nekal types, BASF), alkyl sulfates, in particular fatty alcohol sulfates, lauryl sulfates, and sulfated hexadeca-, heptadeca- and octadecanols, alkylsulfonates, alkyl ether sulfates, in particular fatty alcohol (poly)glycol ether sulfates, alkyl aryl ether sulfates, alkyl polyglycol ether phosphates, polyarylphenyl ether phosphates, alkylsulfosuccinates, olefin sulfonates, paraffin sulfonates, petroleum sulfonates, taurides, sarcosides, fatty acids, alkylnaphthalenesulfonic acids, naphthalene-sulfonic acids, ligninsulfonic acids, condensation products of sulfonated naphthalenes with formaldehyde, condensation products of sulfonated naphthalenes with formaldehyde and phenol and optionally urea and condensation products of phenolsulfonic acid with formaldehyde and urea, lignin sulfite waste liquor, alkyl phosphates, alkyl aryl phosphates, for example tristyryl phosphates, and polycarboxylates such as for example polyacrylates, maleic anhydride/olefin copolymers (for example Sokalan® CP9, BASF), including the alkali metal, alkaline earth, ammonium and amine salts of the aforesaid substances. Preferred anionic surface-active substances are those which bear at least one sulfonate group and in particular the alkali metal and ammonium salts thereof.

Examples of non-ionic surface-active substances are alkylphenol alkoxylates, in particular ethoxylates and ethoxylate-copropoxylates of octylphenol, isooctylphenol, nonylphenol and tributylphenol, di- and tristyrylphenol alkoxylates, alcohol alkoxylates, in particular fatty alcohol ethoxylates and fatty alcohol ethoxylate-copropoxylates, for example alkoxylated isotridecanol, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, ethoxylated fatty acid amides, ethoxylated fatty acid esters, alkyl polyglycosides, ethoxylated alkyl polyglycosides, sorbitan fatty acid esters, ethoxylated sorbitan fatty acid esters, glycerol fatty acid esters, lower molecular weight polyalkylene oxides such as polyethylene glycol, polypropylene oxide, polyethylene oxide co-propylene oxide di- and tri-block copolymers, and mixtures thereof. Preferred nonionic surface-active substances are fatty alcohol ethoxylates, alkyl polyglycosides, glycerol fatty acid esters, castor oil ethoxylates, fatty acid ethoxylates, fatty acid amide ethoxylates, lanolin ethoxylates, fatty acid polyglycol esters, ethylene oxide propylene oxide block copolymers and mixtures thereof.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Protective colloids are typically water-soluble, amphiphilic polymers which unlike the aforesaid surfactants typically have molecular weights over 2,000 daltons (number average). Examples thereof are proteins and denatured proteins such as casein, polysaccharides such as water-soluble starch derivatives and cellulose derivatives, hydrophobically modified starches and celluloses, for example methylcellulose, and also polycarboxylates such as polyacrylic acid, acrylic acid copolymers and maleic acid copolymers (BASF Sokalan types), polyvinyl alcohol (Mowiol types from Clariant), polyalkoxylates, polyvinylpyrrolidone, vinylpyrrolidone copolymers, polyvinyl amines, polyethyleneimines (Lupasol types from BASF) and higher molecular weight polyalkylene oxides such as polyethylene glycol, polypropylene oxides, and polyethylene oxide co-polypropylene oxide di- and tri-block copolymers.

The agrochemical compositions according to the invention can also contain one or more additives modifying the viscosity (rheology modifiers). These are understood in particular to mean substances and substance mixtures which impart modified flow behavior to the formulation, for example a high viscosity in the resting state and low viscosity in the moving state. The nature of the rheology modifier is determined by the nature of the formulation. As examples of rheology modifiers, inorganic substances, for example layer silicates and organically modified layer silicates such as bentonites or attapulgites (for example Atta-clay®, Engelhardt Co.), and organic substances such as polysaccharides and heteropolysaccharides such as Xanthan Gum® (Kelzan® from Kelco Co.), Rhodopol® 23 (Rhone Poulenc) or Veegum® (R.T. Vanderbilt Co.) should be mentioned. The quantity of the viscosity-modifying additives is often 0.1 to 5 wt. %, based on the total weight of the plant protection agent.

Examples of antifoaming agents are the silicone emulsions known for this purpose (Silikon® SRE, Wacker Co. or Rhodorsil® from Rhodia Co.), long-chain alcohols, fatty acids and salts thereof, foam suppressants of the aqueous wax dispersion type, solid foam suppressants (so-called Compounds) and organofluorine compounds and mixtures thereof. The quantity of anti-foaming agent is typically 0.1 to 1 wt. %, based on the total weight of the plant protection agent.

The agrochemical compositions according to the invention may also contain preservatives for stabilization. Suitable preservatives are those based on isothiazol-ones, for example Proxel® from ICI Co., or Acticide® from Thor Chemie Co. or Kathon® MK from Rohm & Hass Co. The quantity of preservative is typically 0.05 to 0.5 wt. %, based on the total weight of the SC.

Aqueous agrochemical compositions, i.e. those with an a aqueous carrier, often contain antifreeze agents. Suitable antifreeze agents are liquid polyols, for example ethylene glycol, propylene glycol or glycerine, and urea. The quantity of antifreeze agent is as a rule 1 to 20 wt. %, in particular 5 to 10 wt. %, based on the total weight of the aqueous plant protection agent.

If the agrochemical composition, which contain the crystalline form(s) A, B, C and/or D of compounds IC.3, are used for seed treatment, they can also contain normal components such as are used for seed treatment, for example in dressing or coating. In addition to the aforesaid components, these include in particular colorants, adhesives, fillers and plasticizers.

All the dyes and pigments usual for such purposes are possible as colorants. Both pigments of low solubility in water and also dyes soluble in water are usable here. As examples, the dyes and pigments known under the names Rhodamin B, C.I. Pigment Red 112 and C.I. Solvent Red 1, Pigment Blue 15:4, Pigment Blue 15:3, Pigment Blue 15:2, Pigment Blue 15:1, Pigment Blue 80, Pigment Yellow 1, Pigment Yellow 13, Pigment Red 48:2, Pigment Red 48:1, Pigment Red 57:1, Pigment Red 53:1, Pigment Orange 43, Pigment Orange 34, Pigment Orange 5, Pigment Green 36, Pigment Green 7, Pigment White 6, Pigment Brown 25, Basic Violet 10, Basic Violet 49, Acid Red 51, Acid Red 52, Acid Red 14, Acid Blue 9, Acid Yellow 23, Basic Red 10, Basic Red 10 and Basic Red 108 may be mentioned. The quantity of colorant will normally not constitute more than 20 wt. % of the formulation and preferably lies in the range from 0.1 to 15 wt. %, based on the total weight of the agrochemical composition.

All binders normally usable in dressings come under consideration as adhesives. Examples of suitable binders include thermoplastic polymers such as poly-vinylpyrrolidone, polyvinyl acetate, polyvinyl alcohol and tylose and also polyacrylates, polymethacrylates, polybutenes, polyisobutenes, polystyrene, polyethylene amines, polyethylene amides, the aforesaid protective colloids, polyesters, polyether esters, polyanhydrides, polyester urethanes, polyester amides, thermoplastic polysaccharides, for example cellulose derivatives such as cellulose esters, cellulose ethers, cellulose ether esters, including methylcellulose, ethylcellulose, hydroxymethylcellulose, carboxymethylcellulose, hydroxypropyl cellulose and starch derivatives and modified starches, dextrins, maltodextrins, alginates and chitosans, and also fats, oils, proteins, including casein, gelatin and zein, gum Arabic and shellac. The adhesives are preferably plant-compatible, i.e. they exhibit no, or no significant, phytotoxic effects. The adhesives are preferably biodegradable. The adhesive is preferably selected such that it acts as a matrix for the active components of the formulation. The quantity of adhesive will normally not constitute more than 40 wt. % of the formulation and preferably lies in the range from 1 to 40 wt. % and in particular in the range from 5 to 30 wt. %, based on the total weight of the agrochemical composition.

In addition to the adhesive, the agrochemical composition for seed treatment can also contain inert fillers. Examples of these are the aforesaid solid carriers, in particular finely divided inorganic materials such as clays, chalk, bentonite, kaolin, talc, perlite, mica, silica gel, diatomaceous earth, quartz powder and montmorillonite but also fine-particle organic materials such as wood flour, cereal flour, active charcoal and the like. The quantity of filler is preferably selected such that the total quantity of filler does not exceed 70 wt. %, based on the total weight of all non-volatile components of the formulation. Often, the quantity of filler lies in the range from 1 to 50 wt. %, based on the total weight of all non-volatile components of the agrochemical composition.

In addition, the agrochemical composition for seed treatment can also contain a plasticizer which increases the flexibility of the coating. Examples of plasticizers are oligomeric polyalkylene glycols, glycerine, dialkyl phthalates, alkylbenzyl phthalates, glycol benzoates and comparable compounds. The quantity of plasticizer in the coating often lies in the range from 0.1 to 20 wt. %, based on the total weight of all non-volatile components of the agrochemical composition.

A preferred embodiment of the invention relates to liquid formulations of the form(s) A, B, C and/or D of compounds IC.3, respectively. In addition to the solid active substance phase, these have at least one liquid phase, in which said forms of compound IC.3 are present in the form of dispersed particles. Possible liquid phases are essentially water and those organic solvents in which the forms of compounds IC.3, respectively, are only slightly soluble, or insoluble, for example those wherein the solubilities of the forms of compounds IC.3, respectively, at 25° C. and 1013 mbar are not more than 1 wt. %, in particular not more than 0.1 wt. %, and especially not more than 0.01 wt. %.

According to a first preferred embodiment, the liquid phase is selected from water and aqueous solvents, i.e. solvent mixtures which in addition to water also contain up to 20 wt. %, preferably however not more than 10 wt. %, based on the total quantity of water and solvent, of one or more organic solvents miscible with water, for example ethers miscible with water such as tetrahydrofuran, methyl glycol, methyl diglycol, alkanols such as isopropanol or polyols such as glycol, glycerine, diethylene glycol, propylene glycol and the like. Such formulations are also referred to below as suspension concentrates (SCs).

Such suspension concentrates contain compound IC.3 in a particulate form, wherein the particles of the form(s) A, B, C and/or D are present suspended in an aqueous phase. The size of the active substance particles, i.e. the size which 90 wt. % of the active substance particles do not exceed, here typically lies below 30 μm, in particular below 20 μm. Advantageously, in the SCs according to the invention, at least 40 wt. % and in particular at least 60 wt. % of the particles have diameters below 2 μm.

In such SCs the quantity of active substance, i.e. the total quantity of tembotrione and of other active substances if necessary, usually lies in the range from 5 to 70 wt. %, in particular in the range from 10 to 50 wt. %, based on the total weight of the suspension concentrate.

In addition to the active substance, aqueous suspension concentrates typically contain surface-active substances, and also if necessary antifoaming agents, thickeners (=rheology modifiers), antifreeze agents, stabilizers (biocides), agents for adjusting the pH and anticaking agents.

Possible surface-active substances are the previously named surface-active substances. Preferably the aqueous plant protection agents according to the invention contain at least one of the previously named anionic surfactants and if necessary one or more nonionic surfactants, if necessary in combination with a protective colloid. The quantity of surface-active substances will as a rule be 1 to 50 wt. %, in particular 2 to 30 wt. %, based on the total weight of the aqueous SCs according to the invention. Preferably the surface-active substances include at least one anionic surface-active substance and at least one nonionic surface-active substance, and the proportion of anionic to nonionic surface-active substance typically lies in the range from 10:1 to 1:10.

Concerning the nature and quantity of the antifoaming agents, thickeners, antifreeze agents and biocides, the same applies as aforesaid.

If necessary, the aqueous SCs according to the invention can contain buffers for pH regulation. Examples of buffers are alkali metal salts of weak inorganic or organic acids, such as for example phosphoric acid, boric acid, acetic acid, propionic acid, citric acid, fumaric acid, tartaric acid, oxalic acid and succinic acid.

According to a second preferred embodiment, the liquid phase consists of non-aqueous organic solvents in which the solubility of form(s) A, B, C and/or D of compound IC.3 at 25° C. and 1013 mbar is not more than 1 wt. %, in particular not more than 0.1 wt. %, and especially not more than 0.01 wt. %. These include in particular aliphatic and cycloaliphatic hydrocarbons and oils, in particular those of plant origin, and also $C_1$-$C_4$ alkyl esters of saturated or unsaturated fatty acids or fatty acid mixtures, in particular the methyl esters, for example methyl oleate, methyl stearate and rape oil methyl ester, but also paraffinic mineral oils and the like. Accordingly, the present invention relates also to agents for plant protection in the form of a non-aqueous suspension concentrate, which will also be referred to below as OD (oil-dispersion). Such ODs contain the form(s) A, B, C and/or D of compounds IC.3, respectively, in particulate form, wherein the particles are present suspended in a non-aqueous phase. The size of the active substance particles, i.e. the size which 90 wt. % of the active substance particles do not exceed, here typically lies below 30 μm, in particular below 20 μm. Advantageously, in the non-aqueous suspension concentrates, at least 40 wt. % and in particular at least 60 wt. % of the particles have diameters below 2 μm.

In such ODs, the quantity of active substance, i.e. the total quantity of compound IC.3 and of other active substances if necessary, usually lies in the range from 10 to 70 wt. %, in particular in the range from 20 to 50 wt. %, based on the total weight of the non-aqueous suspension concentrate.

In addition to the active substance and the liquid carrier, non-aqueous suspension concentrates typically contain surface-active substances, and also if necessary antifoaming agents, agents to modify the rheology and stabilizers (biocides).

Possible surface-active substances are preferably the previously named anionic and nonionic surfactants. The quantity of surface-active substances will as a rule be 1 to 30 wt. %, in particular 2 to 20 wt. %, based on the total weight of the non-aqueous SCs according to the invention. Preferably the surface-active substances include at least one anionic surface-active substance and at least one nonionic surface-active substance, and the proportion of anionic to nonionic surface-active substance typically lies in the range from 10:1 to 1:10.

Form(s) A, B, C and/or D of compounds IC.3, respectively, can also be formulated as solid plant protection agents. These include powder, scattering and dusting agents but also water-dispersible powders and granules, for example coated, impregnated and homogenous granules. Such formulations can be produced by mixing or simultaneous grinding of form(s) A, B, C and/or D of compound IC.3, with a solid carrier and if necessary other additives, in particular surface-active substances. Granules can be produced by binding of the active substances to solid carriers. Solid carriers are mineral earths such as silicic acids, silica gels, silicates, talc, kaolin, limestone, lime, chalk, bole, loess, clay, dolomite, diatomaceous earth, calcium and magnesium sulfate, magnesium oxide, ground plastics, fertilizers such as ammonium sulfate, ammonium phosphate, ammonium nitrate, ureas and plant products such as cereal flour, tree bark, wood and nutshell flour, cellulose powder or other solid carriers. Solid formulations can also be produced by spray drying, if necessary in the presence of polymeric or inorganic drying aids, and if necessary in the presence of solid carriers. For the production of solid formulations of form(s) A, B, C and/or D of compounds IC.3, respectively, extrusion processes, fluidized bed granulation, spray granulation and comparable technologies are suitable.

Possible surface-active substances are the previously named surfactants and protective colloids. The quantity of surface-active substances will as a rule be 1 to 30 wt. %, in particular 2 to 20 wt. %, based on the total weight of the solid formulation according to the invention.

In such solid formulations, the quantity of active substance, i.e. the total quantity of tembotrione and of other active substances if necessary, usually lies in the range from 10 to 70 wt. %, in particular in the range from 20 to 50 wt. %, based on the total weight of the solid formulation.

The following formulation examples illustrate the production of such preparations:

I. Water-Dispersible Powder:
  20 parts by weight of form(s) A, B, C and/or D of compounds IC.3 are mixed well with 3 parts by weight of the sodium salt of diisobutylnaphthalenesulfonic acid, 17 parts by weight of the sodium salt of a ligninsulfonic acid from a sulfite waste liquor and 60 parts by weight of powdered silica gel and ground in a hammer mill. In this manner, a water-dispersible powder which contains the respective form A is obtained.

II. Dusting Agent 5 parts by weight of the form(s) A, B, C and/or D of compounds IC.3 are mixed with 95 parts by weight of finely divided kaolin. In this manner, a dusting agent which contains 5 wt. % of the respective form A is obtained.

III. Non-Aqueous Suspension Concentrate:

20 parts by weight of form(s) A, B, C and/or D of compounds IC.3 are mixed intimately with 2 parts by weight of the calcium salt of dodecylbenzenesulfonic acid, 8 parts by weight of fatty alcohol polyglycol ether, 2 parts by weight of the sodium salt of a phenolsulfonic acid urea formaldehyde condensate and 68 parts by weight of a paraffinic mineral oil. A stable, non-aqueous suspension concentrate of the respective form A is obtained.

IV. Non-Aqueous Suspension Concentrate:

20 parts by weight of form(s) A, B, C and/or D of compounds IC.3 are ground to a fine active substance suspension in an agitator ball mill with the addition of 10 parts by weight of dispersants and wetting agents and 70 parts by weight of a paraffinic mineral oil. A stable, non-aqueous suspension concentrate of the respective form A is obtained. On dilution in water, a stable suspension of the respective form A is obtained. The active substance content in the formulation is 20 wt. %.

V. Aqueous Suspension Concentrate:

10 parts by weight of form(s) A, B, C and/or D of compounds IC.3 are formulated as an aqueous suspension concentrate in a solution of 17 parts by weight of a poly(ethylene glycol)(propylene glycol) block copolymer, 2 parts by weight of a phenolsulfonic acid formaldehyde condensate and about 1 part by weight of other additives (thickeners, foam suppressants) in a mixture of 7 parts by weight of propylene glycol and 63 parts by weight of water.

VI. Aqueous Suspension Concentrate:

20 parts by weight of form(s) A, B, C and/or D of compounds IC.3 are ground to a fine active substance suspension in a stirred ball mill with the addition of 10 parts by weight of dispersants and wetting agents and 70 parts by weight of water. On dilution in water, a stable suspension of the respective form A is obtained. The active substance content in the formulation is 20 wt. %.

VII. Water-Dispersible and Water-Soluble Granules 50 parts by weight of form(s) A, B, C and/or D of compounds IC.3 are finely ground with the addition of 50 parts by weight of dispersants and wetting agents and formulated as water-dispersible or water-soluble granules by means of industrial devices (for example extrusion, spray tower, fluidized bed). On dilution in water, a stable dispersion or solution of the respective form A is obtained. The formulation has an active substance content of 50 wt. %.

VIII. Water-Dispersible and Water-Soluble Powder 75 parts by weight of form(s) A, B, C and/or D of compounds IC.3 are ground in a rotor-stator mill with the addition of 25 parts by weight of dispersants and wetting agents and also silica gel. On dilution in water, a stable dispersion or solution of the respective form A is obtained. The active substance content of the formulation is 75 wt. %.

IX. Gel Formulations:

20 parts by weight of form(s) A, B, C and/or D of compounds IC.3 10 parts by weight of dispersant, 1 part by weight of gelling agent and 70 parts by weight of water or an organic solvent are ground to a fine suspension in a ball mill. On dilution in water, a stable suspension of the respective form A is obtained. The active substance content of the formulation is 20 wt. %.

X. Directly Usable Granules (GR, FG, GG, MG)

0.5 parts by weight of the form(s) A, B, C and/or D of compounds IC.3 are finely ground and combined with 99.5 parts by weight of carriers. Common processes here are extrusion, spray drying or fluidized bed. Granules for direct application with 0.5 wt. % active substance content are thus obtained.

The application of form(s) A, B, C and/or D of compounds IC.3 or the agrochemical composition containing them is effected, if the formulation is not already ready for use, in the form of aqueous spray fluids. These are prepared by dilution of the aforesaid compositions containing form(s) A, B, C and/or D of compounds IC.3 with water. The spray fluids can also contain other components in dissolved, emulsified or suspended form, for example fertilizers, active substances of other herbicidal or growth-regulating active substance groups, other active substances, for example active substances for combating animal pests or phytopathogenic fungi or bacteria, and also mineral salts which are used for the elimination of nutritional and trace element deficiencies, and non-phytotoxic oils and oil concentrates. As a rule, these components are added to the spray fluid before, during or after the dilution of the formulations according to the invention. The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

When employed in plant protection, the amounts of compounds IC.3 applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e. g. by dusting, coating or drenching seed, amounts of compounds IC.3 of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amounts of compounds IC.3 applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners, biopesticides) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

EXAMPLES AND FIGURES

The following figures and examples further illustrate the present invention and do not restrict the invention in any manner.

FIG. 1-1 shows an X-ray powder diffraction diagram of form A of compound IC.3.

FIG. 1-2 shows a DSC trace of form A of compound IC.3, melting point at 114° C.

FIG. 2-1 shows an X-ray powder diffraction diagram of form B of compound IC.3 [(the signals marked with * might be due to minor content of form A)].

FIG. 3-1 shows an X-ray powder diffraction diagram of form C of compound IC.3.

FIG. 4-1 shows an X-ray powder diffraction diagram of form D of compound IC.3.

FIG. 4-2 shows a DSC trace of form D of compound IC.3, melting point at around 55° C.

ANALYTICS

Figures 1, 2:
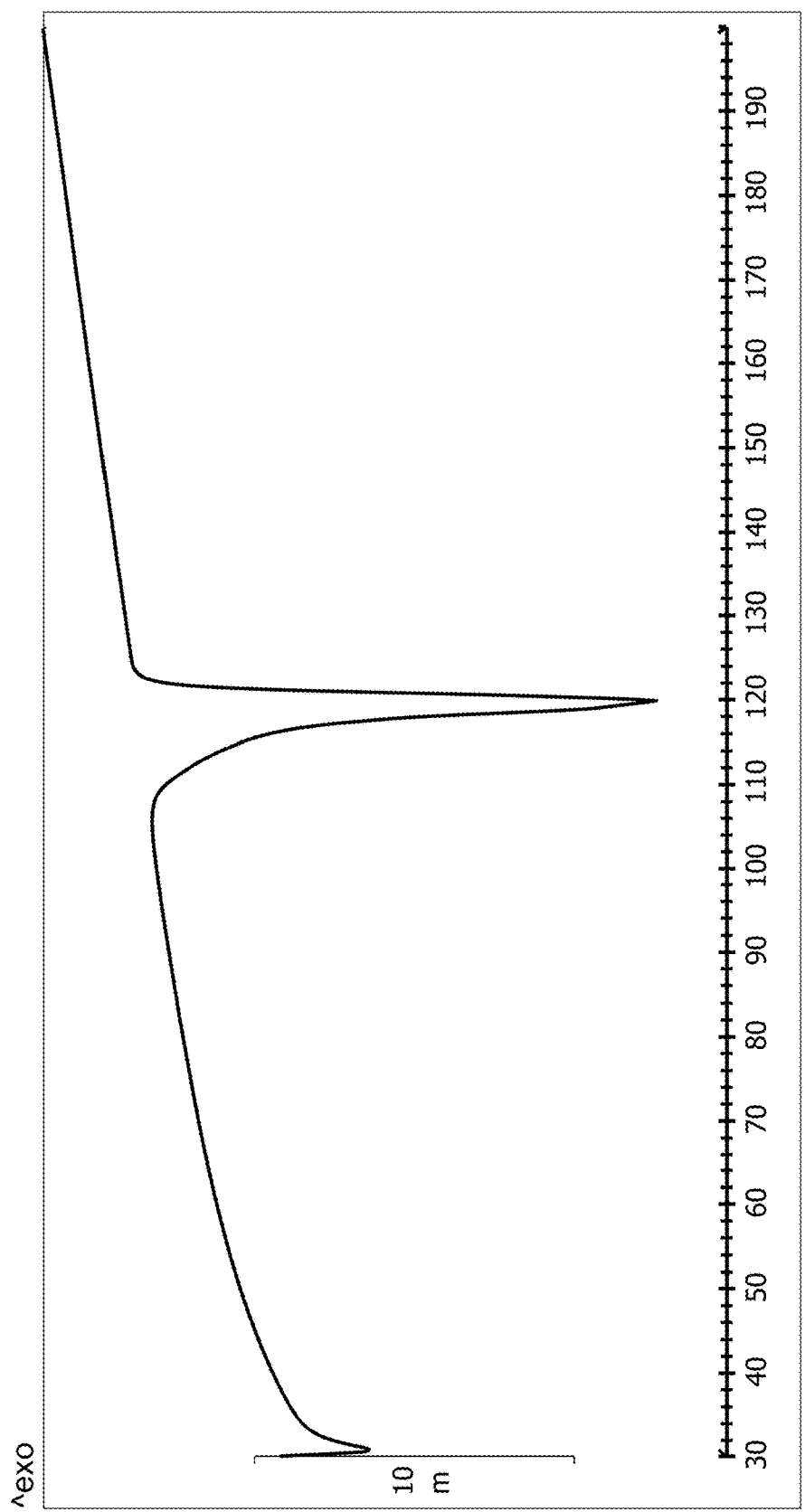
Figures 1, 2:
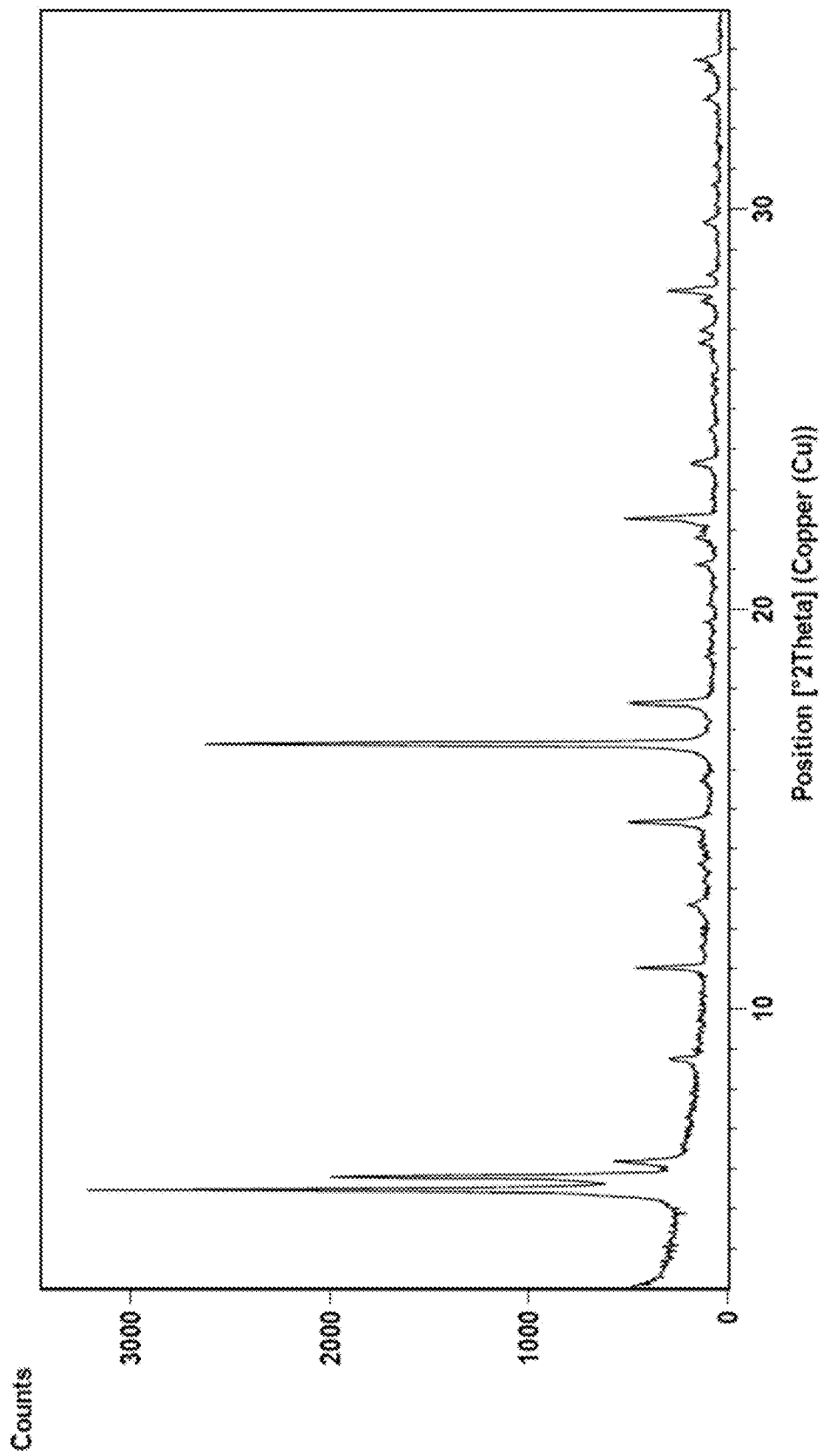
Figures 1, 3:
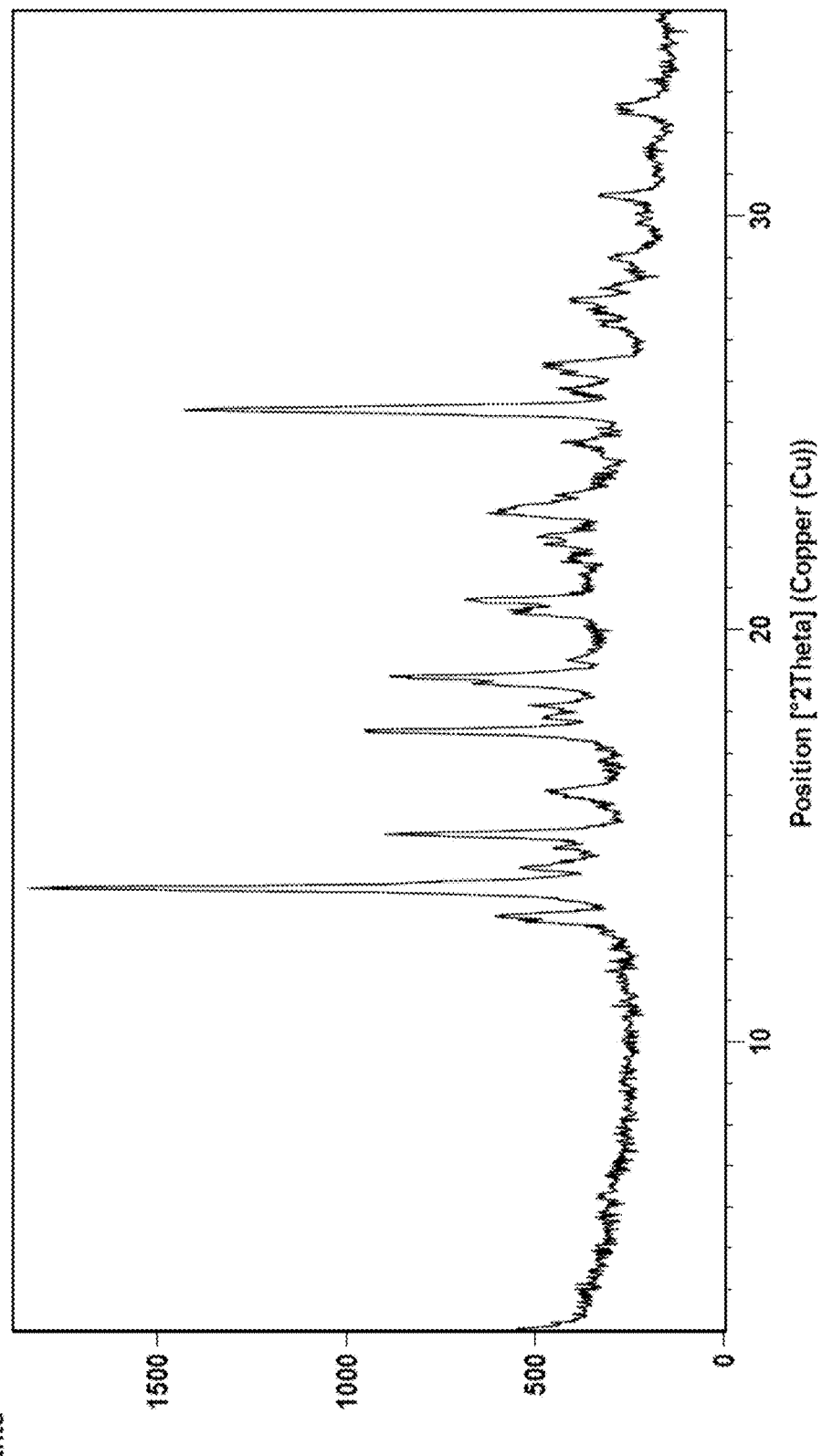
Figures 1, 4:
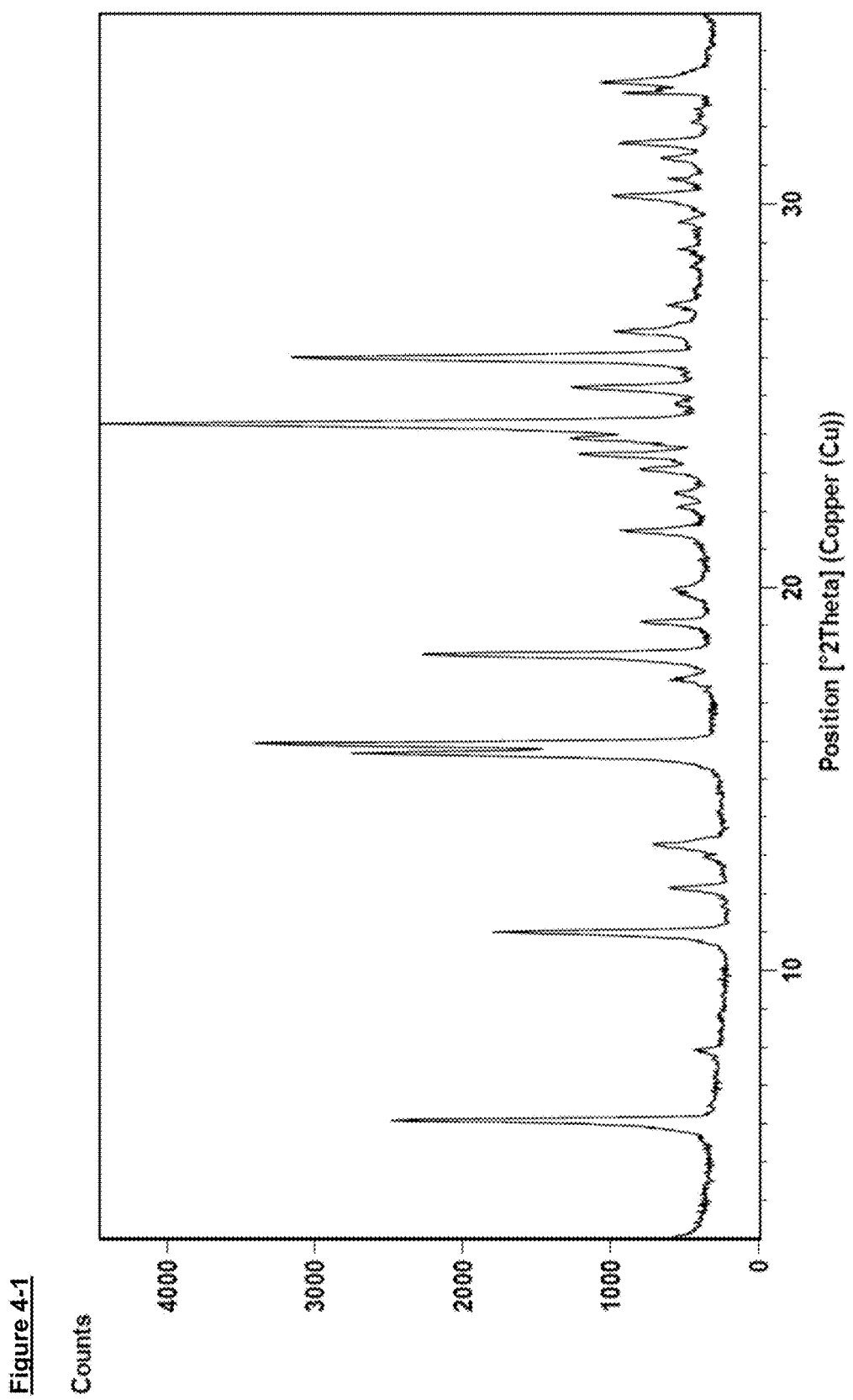
Figures 2, 4:
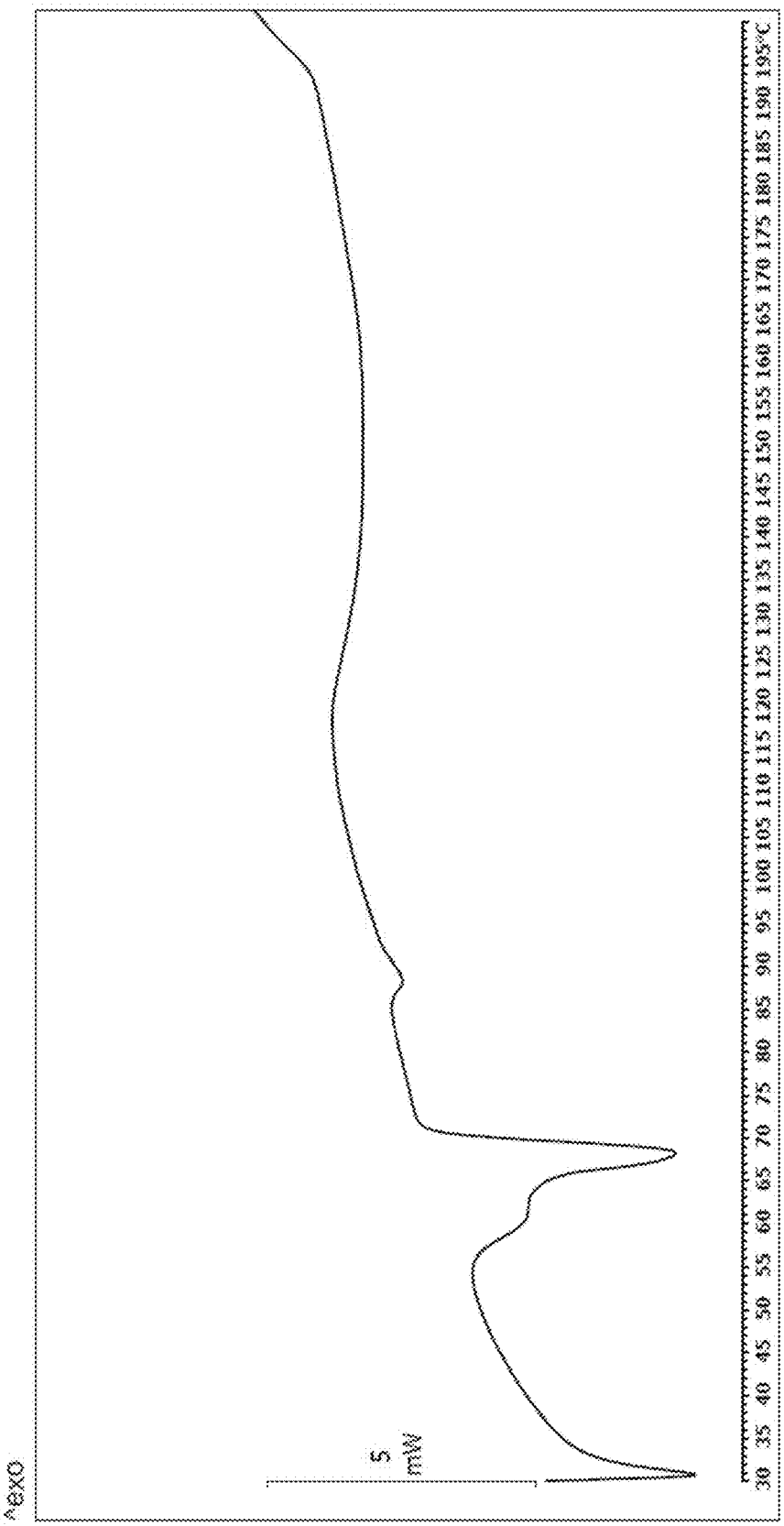

The X-ray powder diffractogram were recorded with a Panalytical X'Pert Pro diffractometer in reflection geometry in the range from 2Θ=3°-35° with a step width of 0.0167° using Cu-Kα radiation (1.54178 Å) at 25° C. The recorded 2Θ values were used to calculate the d values. The intensity of the peaks (linear intensity counts) is plotted versus 2Θ angel (x axis in ° 2Θ).

Single crystal X-ray diffraction data were collected at 100 K on a Bruker AXS CCD Detector, using graphite-monochromated CuKα radiation (λ=1.54178 Å). The structure was solved with direct methods, refined, and expanded by using Fourier techniques with the SHELX software package (G. M. Sheldrick, SHELX-97, University of Göttingen 1997). Absorption correction was performed with SADABS software.

DSC was performed on a Mettler Toledo DSC 823e module. The sample was placed in crimped but vented aluminium pans. Sample size was 3 mg. The thermal behaviour was analysed in the range 30-200° C. by using a heating rate of 10° C./min and a nitrogen stream of 150 mL/min. Melting point values and polymorphic transitions were confirmed by a Mettler Hot Stage in combination with a light microscope.

Examples

The following examples further illustrate the present invention and do not restrict the invention in any manner. Further compounds II and I, respectively, as described above, can be prepared in analogous manner to the following examples.

Example N1—Synthesis of 2-[4-(4-chlorophenoxy)-2-(trifluoromethyl)phenyl]-2-methyl-oxirane 65 g water (3.61 mole) are charged at room temperature. 346.6 g (2.72 mole) dimethyl sulfate are added under stirring. The temperature is increased to 33° C.

180.3 g (2.87 mole) dimethylsulfide are dosed within 90 minutes at 33-39° C. (inside temperature control of the vessel). The first 50 g are dosed slower (in 30 minutes) than the rest due to the highly exothermic reaction. Poststirring period after dosage end: 15 minutes at 38° C.

1-[4-(4-chlorophenoxy)-2-(trifluoromethyl)phenyl]ethanone (1.77 mole) melt (approx. 60° C.) is added at 35° C. 400 g KOH pellets (85 wt-%, 6.06 mole) are added while stirring in 6 portions (30 g, 30 g, 40 g, 100 g, 100 g, 100 g) at 35 to 45° C. Then, it was continued stirring for 2 h at 38° C. A sample of the reaction mixture showed full conversion of the ketone (HPLC).

2500 g water is added at 60° C. and the mixture stirred over 20 minutes. The lower organic product phase is separated and dissolved in DMF. The dimethylsulfide is removed by distillation. 2-[4-(4-chlorophenoxy)-2-(trifluoromethyl)phenyl]-2-methyl-oxirane was determined by quantitative HPLC chromatography in DMF solution (1.75 mole), 99.2% of theory in respect to the ketone starting material.

Example N2—Synthesis of 2-[4-(4-chlorophenoxy)-2-(trifluoromethyl)phenyl]-2-methyl-oxirane 4.8 g water (0.27 mole) were charged at room temperature. 25.5 g (0.2 mole) dimethyl sulfate were added under stirring. The temperature was increased to 33° C.

13.3 g (0.21 mole) dimethylsulfide were dosed within 90 minutes at 33-39° C. (inside temperature control of the vessel). The first 5 g were dosed slower (in 30 minutes) than the rest due to the highly exothermic reaction. Poststirring period after dosage end: 15 minutes at 38° C.

1-[4-(4-chlorophenoxy)-2-(trifluoromethyl)phenyl]ethanone (0.13 mole) melt (at approx. 60° C.) was added at 35° C. 31 g KOH pellets, 85 wt-% (0.47 mole) were added while stirring in one portion at 35 to 45° C. Then, it was continued stirring for 1.5 h at 40° C. A sample of the reaction mixture showed full conversion of the ketone (HPLC).

220 g water was added at 41° C. and the mixture was heated to 60° C. over 10 minutes. The agitor was stopped and the lower organic product phase was separated, dissolved in DMF and the dimethylsulfide removed by distillation. 2-[4-(4-chlorophenoxy)-2-(trifluoromethyl)phenyl]-2-methyl-oxirane was determined by quantitative HPLC chromatography in 50 g DMF solution (0.122 mole), 96.9% of theory in respect to the ketone starting material.

Example N3—Synthesis of 2-[4-(4-chlorophenoxy)-2-(trifluoromethyl)phenyl]-2-methyl-oxirane 40 g (0.314 mole) dimethyl sulfate were charged at room temperature and 8 g (0.444 mole) water were added under stirring.

22.5 g (0.359 mole) dimethylsulfide were dosed in at 20-44° C. within approximately 60 minutes (inside temperature control of the vessel). Poststirring period after dosage end: 1 h at 37° C. and over night at room temperature.

43 g (0.651 mole, 85% w/w) KOH pellets were added as 25° C. (exotherm, temperature increase to 32° C.). Afterwards 1-[4-(4-chlorophenoxy)-2-(trifluoromethyl)phenyl]ethanone (0.13 mole) melt (approx. 60° C.) was dosed at 30-43° C. during 15 minutes. Then, stirring was continued for 2 h at 39° C. A sample of the reaction mixture showed full conversion of the ketone (HPLC).

310 g water was added at 38° C. and the mixture was heated to 60° C. over 10 minutes. The agitor was stopped and the lower organic product phase was separated and dissolved in 33.7 g DMF. 2-[4-(4-chlorophenoxy)-2-(trifluoromethyl)phenyl]-2-methyl-oxirane was determined by quantitative HPLC chromatography in solution with 96.4% (0.122 mole) in respect to the ketone starting material.

Example N4—Synthesis of 2-[4-(4-chlorophenoxy)-2-(trifluoromethyl)phenyl]-2-methyl-oxirane 15 g dimethylsulfide (0.239 mole) and 5.4 g water (0.3 mole) were charged at room temperature. The temperature was increased to 35° C.

26 g (0.204 mole) dimethyl sulfate were added under stirring at 35-39° C. over 30 minutes. Poststirring period after dosage end: 3 h at 36° C.

1-[4-(4-chlorophenoxy)-2-(trifluoromethyl)phenyl]ethanone (0.13 mole) ° C. was added as melt. 31 g KOH pellets (85 wt.-%, 0.47 mole) were dosed slowly starting at 20° C. Due to the exothermic reaction, temperature increased to 35° C. Then, it was continued stirring for 2 h at 37° C. A sample of the reaction mixture showed full conversion of the ketone (HPLC).

205 g water was added at 37° C. and the mixture stirred over 10 minutes. The lower aqueous phase was separated at 30° C. The organic product phase was concentrated by distillation for removal of the dimethylsulfide. The residue was dissolved in 50 g DMF and the product amount of 2-[4-(4-chlorophenoxy)-2-(trifluoromethyl)phenyl]-2-methyl-oxirane was determined by quantitative HPLC chromatography in DMF solution with 98.4% in respect to the ketone starting material (0.128 mole).

Example M1—(Preparation 2-[4-(4-chlorophenoxy)-2-(trifluoromethyl)phenyl]-1-(1,2,4-triazol-1-yl)propan-2-ol 109 g (51.3 wt-% in DMF; 0.1701 mole) 2-[4-(4-chlorophenoxy)-2-(trifluoromethyl)phenyl]-2-methyl-oxirane were diluted with 105.6 g DMF at room temperature. 15.6 g (98 wt-%; 0.221 mole) of 1,2,4-triazole and 3.47 g (0.085 mole) NaOH flakes were added under stirring. The reaction mixture was heated to 125-126° C. and then stirred for 5 h in total at this temperature. A HPLC-sample showed complete conversion to the desired product (ratio triazol-1-yl/triazol-4-yl about 10:1). About 93% of the DMF was evaporated at 125° C./300-60 mbar. To the concentrated reaction mixture, 150 g butyl acetate and 92.3 g water were added and the mixture stirred over 10 minutes. Then, the aqueous phase was separated at 80° C.

The organic phase was concentrated at 85° C./400-130 mbar by 50% (distillate of 117.6 g butyl acetate). The solution was cooled to 60° C. and seeded with product and stirred at this temperature over 30 minutes so that the product crystallized slowly. Further cooling to 0° C. with a rate of 7.5° K/h followed by suction filtration of the product, washing with 42.8 g n-butyl acetate at 0° C. and drying in a drying cabinet at 55° C./15 mbar led to 52.1 g of product (78.1% of the theory, with a purity of 98.9% determined by quantitative HPLC analytics. Triazol-4-yl-Isomer: 0.74%).

Example M2—Preparation 2-[4-(4-chlorophenoxy)-2-(trifluoromethyl)phenyl]-1-(1,2,4-triazol-1-yl)propan-2-ol 50 g (83 wt-%, 0.1263 mole) 2-[4-(4-chlorophenoxy)-2-(trifluoromethyl)phenyl]-2-methyl-oxirane were dissolved in 102.9 g DMF at room temperature. 11.6 g (98 wt-%; 0.164 mole) of 1,2,4-triazole and 11.68 g (0.095 mole) 4-dimethylaminopyridine were added under stirring. The reaction mixture was heated to 129° C. over 22 h. A HPLC-sample showed complete conversion to the desired product. The crude yield was determined by quantitative HPLC of the final reaction mixture (172.4 g with a content of 24.9%) with 85.6%.

165 g of the reaction mixture were distilled without using a column (13 mbar, end temperature 150° C.). The first fractions contained the major part of the DMAP. Recycling of this base using a column should therefore be feasible. The residue of the distillation contained the desired product with a purity of 83.6%. Crystallization from an organic solvent like toluene or n-butyl acetate is expected to improve the purity significantly according to the experience with the compound.

Example M3: 2-[4-(4-chlorophenoxy)-2-(trifluoromethyl)phenyl]-3-methyl-1-(1,2,4-triazol-1-yl)butan-2-ol 2-[4-(4-chlorophenoxy)-2-(trifluoromethyl)phenyl]-2-isopropyl-oxirane (92.9 g, 76.9 wt-%, 0.217 mole) were dissolved in 180.6 g DMF. To this solution, 27.4 g (98 wt-%; 0.391 mole) triazole and 4.7 g (0.117 mole) NaOH powder were added at 25° C. After heating to 125° C. the reaction mixture was stirred at this temperature for 22.5 h in total. A HPLC-sample showed still remaining oxirane and a ratio of the triazole products of 10.3:1 (triazole-1-yl/triazole-4-yl). The addition of additional 0.3 eq triazole and stirring for another 2 h at 125° C. did not improve the conversion. About 79% of the DMF were evaporated at up to 60° C./4 mbar. 413 g toluene and 205 g water were added to the concentrated reaction mixture at 80° C. Then, the aqueous phase was separated at 55° C. The toluene solution was concentrated at up to 90° C./40 mbar until a residue of 108 g remained. 111 g methanol were added to the residue at 60° C. The solution obtained was cooled down to −1° C. with a rate of 5° C./h. Seed crystals were added at 45° C. The suspension of solids was easily stirrable and was separated by suction filtration and washed 1 time with 25 g of fresh and cold (0° C.) methanol. The solid compound was dried at 55° C. and 50 mbar. Yield: 64.8 g (96.9 wt-%; ratio triazole-1-yl/triazole-4-yl about 100:1); 73% of the theory. The crystals contained residual methanol as detected be $^1$H-NMR; Melting point: 114 to 115° C.

The invention claimed is:
1. A process for the preparation of the compounds of formula II

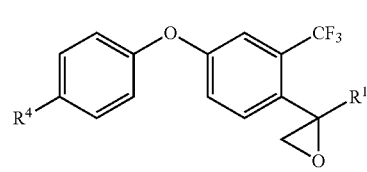

wherein
$R^1$ is $C_1$-$C_6$-alkyl or $C_3$-$C_8$-cycloalkyl; and
$R^4$ is F or Cl
comprising the following step:
(i) reacting an oxo compound of the formula III

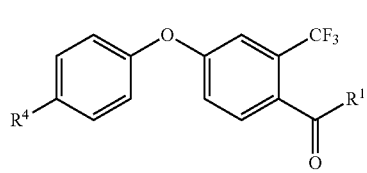

with dimethyl sulfide $(CH_3)_2S$ and dimethylsulfate $(CH_3)_2SO_4$, forming the reagent IV, trimethylsulfonium methylsulfate $[(CH_3)_3S^+ \ CH_3SO_4^-]$, in aqueous solution in the presence of potassium hydroxide (KOH), wherein dimethyl sulfide and dimethyl sulfate are used in a molar ratio of 1:1 to 2:1, and wherein at most 10 weight-% organic solvent in relation to the amount of compound III, are added.

2. The process of claim 1, wherein at least 2 equivalents of base per 1 equivalent of compound III are used.

3. A process for making the compound of formula I, comprising the following step:
(i) preparing a compound of formula II

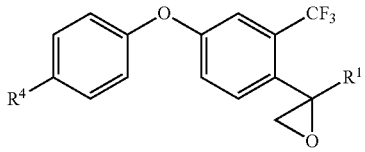

using the process of claim 1,
(ii) reacting the oxirane of the formula II resulting from step (i) with 1H-1,2,4-triazole and a base, resulting in compounds of formula I

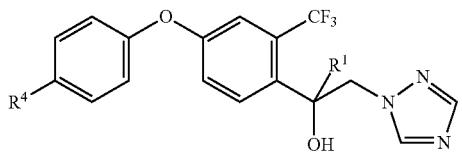

wherein the variables $R^1$ and $R^4$ are as defined in claim 1.

4. The process of claim 3, wherein an inorganic base is used and less than 1 equivalent of said inorganic base is used per 1 equivalent of compound II.

5. The process of claim 3, wherein the product resulting from step (ii) is crystallized from toluene and/or ortho-xylene and/or an aliphatic alcohol and/or carbonic acid ester.

6. The process of claim 5, wherein the aliphatic alcohol is selected from the group consisting of methanol, ethanol, n-propanol, iso-propanol, n-butanol, isobutanol and mixtures thereof.

7. The process of claim 5, wherein n-butyl acetate or ethyl acetate or a mixture thereof is used for crystallization.

* * * * *